(12) United States Patent
Malherbe et al.

(10) Patent No.: US 7,390,903 B2
(45) Date of Patent: Jun. 24, 2008

(54) THIENO-PYRIDINE DERIVATIVES AS ALLOSTERIC ENHANCERS OF THE GABA$_B$ RECEPTORS

(75) Inventors: Parichehr Malherbe, Muttenz (CH); Raffaello Masciadri, Basel (CH); Roger David Norcross, Olsberg (CH); Hasane Ratni, Habsheim (FR); Andrew William Thomas, Birsfelden (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/301,696

(22) Filed: Dec. 13, 2005

(65) Prior Publication Data
US 2006/0135552 A1 Jun. 22, 2006

(30) Foreign Application Priority Data
Dec. 17, 2004 (EP) ................ 04106665

(51) Int. Cl.
C07D 498/02 (2006.01)
(52) U.S. Cl. .................................... 546/114
(58) Field of Classification Search ........... 546/114
See application file for complete search history.

(56) References Cited

U.S. PATENT DOCUMENTS

| 6,313,146 B1 | 11/2001 | Van Wagenen et al. |
| 6,649,626 B1 | 11/2003 | Dodd et al. |

FOREIGN PATENT DOCUMENTS

| EP | 0 334 491 | 9/1989 |
| EP | 0 419 247 | 3/1991 |
| WO | WO 96/14319 | 5/1996 |
| WO | WO 01/29030 | 4/2001 |
| WO | WO 01/56990 | 8/2001 |
| WO | WO 03/090731 | 11/2003 |

OTHER PUBLICATIONS

Abdel-Rahman, et al., STN Accession No. 2002:577450; Document No. 137:294919; abstract of Journal of the Chinese Chemical Society, (2002), 49(2), 223-231.*
Hill et al., Nature, 290, pp. 149-152, (1981).
Billinton et al. Trends in Neurosci., 24, 277-282, (2001).
Bowery et al., Pharmacol. Rev.. 54, pp. 247-264, (2002).
Vacher et al., Curr. Drug Targets, CNS Neurol. Disord. 2, pp. 248-259, (2003).
Bettler et al., Physiol Rev. 84, pp. 835-867, (2004).
Kaupmann et al., Nature, 386, pp. 239-246, (1997).
Kaupmann et al., Nature, 396, pp. 683-687, (1998).
Pin et al., Pharmaco.. Ther. 98, pp. 325-354, (2003).
Galvez et al., J. Biol. Chem., 275, pp. 41166-41174, (2000).
Havlickova et al., Mol. Pharmacol. 62, pp. 343-350, (2002).
Kniazeff et al.,J. Neurosci., 22, pp. 7352-7361, (2002).
Schuler et al., Neuron, 31, pp. 47-58, (2001).
Peters et al., Neurogenetics, 2, pp. 47-54, (1998).
Mondabon et al., Am. J. Med. Genet 122B/1, p. 134, (2003).
Gassmann et al., J Neurosci. 24, pp. 6086-6097, (2004).
Misgeld et al., Prog. Neurobiol. 46, pp. 423-462, (1995).
Enna et al., Life Sci, 62, pp. 1525-1530, (1998).
McCarson et al., Neuropharmacology, 38, pp. 1767-1773, (1999).
Brebner et al., Neuropharmacology, 38, pp. 1797-1804, (1999).
Paterson et al., Psychopharmacology, 172, pp. 179-186, (2004).
Breslow et al., Am. J. Psychiatry, 146, pp. 353-356, (1989).
Drake et al., Ann. Pharmacother. 37., pp. 1177-1181, (2003).
Bortolato et al., Psychopharmacology, 171, pp. 322-330, (2004).
Urwyler et al., Mol. Pharmacol., 60, pp. 963-971, (2001).
Pin et al., Mol. Pharmacol.,60, pp. 881-884, (2001).
Binet et al., J Biol Chem., 279, pp. 29085-29091, (2004).
Wigger et al., Neuropsychopharmacology, pp. 1-14, (2004).
Urwyler et al., J. Pharmacol. Exp. Ther., 307, pp. 322-330, (2003).
Cryan et al., J Pharmacol Exp Ther., 310, pp. 952-963, (2004).
Smith et al., Psychopharmacology, 173, pp. 105-111, (2004).
Knoflach et al., Proc. Natl. Acad. Sci., USA, 98, pp. 13402-13407, (2001).
Wichmann et al., Il Farmaco, 57, pp. 989-992, (2002).
Hammerland et al., Mol. Pharmacol., 53, pp. 1083-1088, (1998).
O'Brien et al., J. Pharmaco. Exp. Ther., 309, pp. 568-577 (2004).
Schaffhauser et al., Mol. Pharmacol., 64, pp. 798-810, (2003).

* cited by examiner

*Primary Examiner*—D. Margaret Seaman
*Assistant Examiner*—Nizal S Chandrakumar
(74) *Attorney, Agent, or Firm*—George W. Johnston; Patricia S. Rocha-Tramaloni; Kimberly J. Prior

(57) ABSTRACT

The present invention relates to compounds of formula I

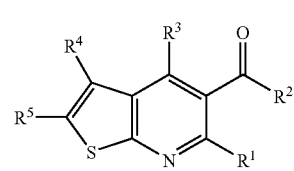

wherein $R^1$, $R^2$, $R^3$, $R^4$, and $R^5$ are as defined in the specification. Compounds of the invention are active on the GABAB receptor and are useful for treating a variety of CNS disorders, including anxiety, depression, epilepsy, schizophrenia, cognitive disorders, spasticity-and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders and gastro-intestinal disorders.

28 Claims, No Drawings

THIENO-PYRIDINE DERIVATIVES AS ALLOSTERIC ENHANCERS OF THE GABA$_B$ RECEPTORS

PRIORITY TO RELATED APPLICATIONS

This application claims the benefit of European Application No. 04106665.5, filed Dec. 17, 2004, which is hereby incorporated by reference in its entirety.

BACKGROUND OF THE INVENTION

γ-Aminobutyric acid (GABA), the most abundant inhibitory neurotransmitter, activates both ionotropic GABA$_{A/C}$ and metabotropic GABA$_B$ receptors (Hill and Bowery, Nature, 290, 149-152, 1981). GABA$_B$ receptors that are present in most regions of the mammalian brain on presynaptic terminals and postsynaptic neurons are involved in the fine-tuning of inhibitory synaptic transmission. Presynaptic GABA$_B$ receptors through modulation of high-voltage activated Ca$^{2+}$ channels (P/Q- and N-type) inhibit the release of many neurotransmitters. Postsynaptic GABA$_B$ receptors activates G-protein coupled inwardly rectifying K+(GIRK) channel and regulates adenylyl cyclase (Billinton et al., Trends Neurosci., 24, 277-282, 2001; Bowery et al., Pharmacol. Rev. 54, 247-264, 2002). Because the GABA$_B$ receptors are strategically located to modulate the activity of various neurotransmitter systems, GABA$_B$ receptor ligands hence could have potential therapeutics in the treatment of anxiety, depression, epilepsy, schizophrenia and cognitive disorders (Vacher and Bettler, Curr. Drug Target, CNS Neurol. Disord. 2, 248-259, 2003; Bettler et al., Physiol Rev. 84, 835-867, 2004).

Native GABA$_B$ receptors are heteromeric structures composed of two types of subunits, GABA$_B$R1 and GABA$_B$R2 subunits (Kaupmann et al., Nature, 386, 239-246, 1997 and Nature, 396, 683-687, 1998). The structure of GABA$_B$R1 and R2 show that they belong to a family of G-protein coupled receptors (GPCRs) called family 3. Other members of the family 3 GPCRs include the metabotropic glutamate (mGlu1-8), Calcium-sensing, vomeronasal, pheromone and putative taste receptors (Pin et al., Pharmaco. Ther. 98, 325-354, 2003). The family 3 receptors (including GABA$_B$ receptors) are characterized by two distinctly separated topological domains: an exceptionally long extracellular amino-terminal domain (ATD, 500-600 amino acids), which contains a venus flytrap module for the agonist binding (orthosteric site) (Galvez et al., J. Biol. Chem., 275, 41166-41174, 2000) and the 7TM helical segments plus intracellular carboxy-terminal domain that is involved in receptor activation and G-protein coupling. The mechanism of receptor activation by agonist in GABA$_B$R1R2 heterodimer is unique among the GPCRs. In the heteromer, only GABA$_B$R1 subunit binds to GABA, while the GABA$_B$R2 is responsible for coupling and activation of G-protein (Havlickova et al., Mol. Pharmacol. 62, 343-350, 2002; Kniazeff et al., J. Neurosci., 22, 7352-7361, 2002).

Schuler et al., Neuron, 31, 47-58, 2001 have demonstrated that the GABA$_B$R1 knock-out (KO) mice exhibit spontaneous seizures and hyperalgesia. These KO mice have lost all the biochemical and electrophysiological GABA$_B$ responses. Interestingly, the GABA$_B$R1 KO mice were more anxious in two anxiety paradigm, namely the light-dark box (decreased time in light) and staircase tests (decreased rears and steps climbed). They showed a clear impairment of passive avoidance performance model indicating impaired memory processes. The GABA$_B$R1 KO also displayed increased hyperlocomotion and hyperactivity in new environment. The GABA$_B$R1 gene is mapped to chromosome 6p21.3, which is within the HLA class I, a region with linkage for schizophrenia, epilepsy and dyslexia (Peters et al., Neurogenetics, 2, 47-54, 1998). Mondabon et al., Am. J. Med. Genet 122B/1, 134, 2003 have reported about a weak association of the Ala20Val polymorphism of GABA$_B$R1 gene with schizophrenia. Moreover, Gassmann et al., J Neurosci. 24, 6086-6097, 2004 has shown that GABA$_B$R2KO mice suffer from spontaneous seizures, hyperalgesia, hyperlocomotor activity and severe memory impairment, comparable to GABA$_B$R1KO mice. Therefore, heteromeric GABA$_B$ R1R2 receptors are responsible for these phenotypes.

Baclofen (Lioresalθ, β-chlorophenyl GABA), a selective GABA$_B$ receptor agonist with EC$_{50}$=210 nM at native receptor, is the only ligand, which has been used since 1972 in clinical study for the treatment of spasticity and skeletal muscle rigidity in patients following spinal cord injury, multiple sclerosis, amyotrophic lateral sclerosis, cerebral palsy. Most of the preclinical and clinical studies conducted with baclofen and GABA$_B$ receptor agonists were for the treatment of neuropathic pain and craving associated with cocaine and nicotine (Misgeld et al., Prog. Neurobiol. 46, 423-462, 1995; Enna et al., Life Sci, 62, 1525-1530, 1998; McCarson and Enna, Neuropharmacology, 38, 1767-1773, 1999; Brebner et al., Neuropharmacology, 38, 1797-1804, 1999; Paterson et al., Psychopharmacology, 172, 179-186, 2003). In panic disorder patients, Baclofen was shown to be significantly effective in reducing the number of panic attacks and symptoms of anxiety as assessed with the Hamilton anxiety scale, Zung anxiety scale and Katz-R nervousness subscale (Breslow et al., Am. J. Psychiatry, 146, 353-356, 1989). In a study with a small group of veterans with chronic, combat-related post-traumatic stress disorder (PTSD), baclofen was found to be an effective and well-tolerated treatment. It resulted in significant improvements in the overall symptoms of PTSD, most notably the avoidance, emotional numbing and hyperarousal symptoms and also in reduced accompanying anxiety and depression (Drake et al., Ann. Pharmacother. 37, 1177-1181, 2003). In preclinical study, baclofen was able to reverse the reduction in prepulse inhibition (PPI) of the acoustic startle response induced by dizocilpine, but not by apomorphine in rat PPI model of psychosis (Bortolato et al., Psychopharmacology, 171, 322-330, 2004). Therefore, GABA$_B$ receptor agonist has a potential in the pharmacological therapy of psychotic disorders. Unfortunately, Baclofen has a number of side-effects including the poor blood-brain-barrier penetration, very short duration of action and narrow therapeutic window (muscle relaxation, sedation and tolerance) that limit its utility.

Urwyler et al., Mol. Pharmacol., 60, 963-971, 2001 have reported on a novel class of GABA$_B$ receptor ligands, called positive allosteric modulators, CGP7930 [2,6-di-tert-butyl-4-(3-hydroxy-2,2-dimethyl-propyl)-phenol] and its aldehyde analogue CGP13501. These ligands have no effect on their own at GABA$_B$ receptors, but in concert with endogenous GABA, they increase both the potency and maximal efficacy of GABA at the GABA$_B$R1R2 (Pin et al., Mol. Pharmacol., 60, 881-884, 2001). Interestingly, recent study with CGP7930 (Binet et al., J Biol. Chem., 279, 29085-29091, 2004) has shown that this positive modulator activates directly the seven transmembrane domains (7TMD) of GABA$_B$R2 subunit. Mombereau et al., Neuropsychopharmacology, 1-13, 2004 have recently reported on the anxiolytic effects of acute and chronic treatment with the GABA$_B$ receptor positive modulator, GS39783 (N,N_-dicyclopentyl-2-methylsulfanyl-5-nitro-pyrimidine-4,6-diamine) (Urwyler et al., *J. Pharmacol. Exp. Ther.*, 307, 322-330, 2003) in the light-dark box and elevated zero maze test models of anxiety. No tolerance after chronic treatment (21 days) with GS39783 (10 mg/kg, P.O., once daily) was observed. Because the $GABA_B$ enhancers have no effect on receptor activity in the absence of GABA, but do enhance allosterically the affinity of the $GABA_B$ receptor for the endogenous GABA, it is expected that these ligands should have an improved side effect profile as compared to baclofen. Indeed, GS39783 at 0.1-200 mg/kg, PO had no effect on spontaneous locomotor activity, rotarod, body temperature and traction test in comparison to baclofen, which showed these side effects at 2.5-15 mg/kg, PO. GS39783 did not have any effect on cognition performance as assessed by passive avoidance behavioral test in mice and rats. Furthermore, GS39783 exhibited anxiolytic-like effects in the elevated plus maze (rat), elevated zero maze (mice and rats), and the stress-induced hyperthermia (mice) test paradigms. Therefore, GS39783 represents a novel anxiolytic without side-effects associated with baclofen or benzodiazepines (Cryan et al., *J Pharmacol Exp Ther.*, 310, 952-963, 2004). The preclinical investigation with the CGP7930 and GS39783 has shown that both compounds were effective at deceasing cocaine self-administration in rats (Smith et al., *Psychopharmacology*, 173, 105-111, 2004). The positive modulator, CGP7930 has also been preclinically studied for the treatment of Gastro-Esophageal Reflux Disease (GERD) and was found to be effective (WO 03/090731, Use of $GABA_B$ receptor positive modulators in gastro-intestinal disorders).

Positive allosteric modulators have been reported for other family 3 GPCRs including mGlu1 receptor (Knoflach et al, *Proc. Natl. Acad. Sci., USA*, 98, 13402-13407, 2001; Wichmann et al., *Farmaco*, 57, 989-992, 2002), Calcium-sensing receptor (NPS R-467 and NPS R-568) (Hammerland et al., *Mol. Pharmacol.*, 53, 1083-1088, 1998) (U.S. Pat. No. 6,313, 146), mGlu2 receptor [LY487379, N-(4-(2-methoxyphenoxy)-phenyl-N-(2,2,2-trifluoroethylsulfonyl)-pyrid-3-ylmethylamine and its analogs] (WO 01/56990, Potentiators of glutamate receptors) and mGlu5 receptor (CPPHA, N-{4-chloro-2-[(1,3-dioxo-1,3-dihydro-2H-isoindol-2-yl)methyl] phenyl}-2-hydroxybenzamide) (O'Brien et al., *J. Pharmaco. Exp. Ther.*, 27, Jan. 27, 2004). Interestingly, it has been demonstrated that these positive modulators bind to a novel allosteric site located within the 7TMD region, thereby enhancing the agonist affinity by stabilizing the active state of the 7TMD region (Knoflach et al., *Proc. Natl. Acad. Sci., USA* 98, 13402-13407, 2001; Schafjhauser et al., *Mol. Pharmacol.*, 64, 798-810, 2003). Moreover, the NPS R-467, NPS R-568 (Tecalcet) and related compounds represent the first positive allosteric modulators that entered the clinical trails due to their allosteric mode of action.

SUMMARY OF THE INVENTION

The present invention provides compounds of formula I

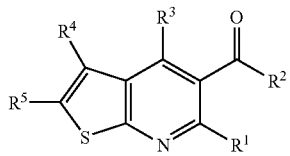

wherein
$R^1$ is hydrogen, $C_1$-$C_7$-alkyl, $C_1$-$C_7$-haloalkyl, or $C_3$-$C_8$-cycloalkyl;

$R^2$ is $C_1$-$C_7$-alkyl, $C_1$-$C_7$-haloalkyl, $C_3$-$C_8$-cycloalkyl, optionally substituted aryl or optionally substituted heteroaryl having 5 to 9 ring atoms, wherein the substituents are selected from the group consisting of halo, $C_1$-$C_7$-alkoxy, $C_1$-$C_7$-haloalkyl, $C_1$-$C_7$-haloalkoxy, $C_1$-$C_7$-alkylsulfonyl, and —C(O)O—$C_1$-$C_7$-alkyl;

$R^3$ is —$NR^aR^b$; optionally substituted heterocycloalkyl having 3 to 8 ring atoms; optionally substituted aryl or optionally substituted heteroaryl having 5 to 9 ring atoms, wherein the substituents are selected from the group consisting of halo, $C_1$-$C_7$-alkoxy, $C_1$-$C_7$-haloalkyl, $C_1$-$C_7$-haloalkoxy, $C_1$-$C_7$-alkylsulfonyl, and —C(O)O—$C_1$-$C_7$-alkyl;

$R^4$ is hydrogen or $C_1$-$C_7$-alkyl; and $R^5$ is hydrogen, halo, $C_1$-$C_7$-alkyl, $C_2$-$C_7$-alkenyl, —$NR^aR^b$; optionally substituted aryl or optionally substituted heteroaryl having 5 to 9 ring atoms, wherein the substituents are selected from the group consisting of halo, cyano, $C_1$-$C_7$-alkyl, $C_1$-$C_7$-haloalkyl, $C_1$-$C_7$-alkoxy, $C_1$-$C_7$-haloalkoxy, $C_1$-$C_7$-alkylsulfonyl, and —C(O)O—$C_1$-$C_7$-alkyl;

or $R^5$ together with $R^4$ forms a ring selected from the group consisting of $C_5$-$C_7$-cycloalkyl, heterocycloalkyl having 5 to 7 ring atoms, phenyl, pyridinyl, and pyrimidinyl each of which are optionally substituted or by one or more halo, cyano, $C_1$-$C_7$-alkylsulfonyl, $C_1$-$C_7$-alkyl, $C_1$-$C_7$-haloalkyl, $C_1$-$C_7$-alkoxy, $C_1$-$C_7$-haloalkoxy, or —C(O)O—$C_1$-$C_7$-alkyl;

$R^a$ and $R^b$ are each independently $C_1$-$C_7$-alkyl, or $R^a$ and $R^b$, together with the nitrogen atom to which they are attached, form an heterocycloalkyl group having 3 to 8 ring atoms which is optionally substituted by one or more halo, $C_1$-$C_7$-alkyl, $C_1$-$C_7$-alkoxy, hydroxy, phenyl or di($C_1$-$C_7$)alkylamino;

and a pharmaceutically acceptable salt thereof.

The invention also provides pharmaceutical compositions comprising compounds of the invention and methods for the preparations of such compounds and compositions.

The compounds of the invention are active on the $GABA_B$ receptor and have valuable therapeutic properties. The invention further provides methods for the treatment of disorders such as anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders and gastrointestinal disorders.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "Aryl" means a monovalent cyclic aromatic hydrocarbon moiety containing preferably from 6 to 10 carbon atoms or "$C_6$-$C_{10}$-aryl". Preferred aryls include, but are not limited to, optionally substituted phenyl, and naphthyl as well as those specifically illustrated by the examples hereinbelow.

"$C_1$-$C_7$-alkyl" denotes a straight- or branched-carbon chain group containing from 1 to 7 carbon atoms, preferably 1 to 4 carbon atoms. Examples of such groups are are methyl, ethyl, propyl, isopropyl, isobutyl, sec-butyl, tert-butyl, pentyl, and n-hexyl as well as those specifically illustrated by the examples herein below.

"$C_2$-$C_7$-alkenyl" denotes a straight- or branched-carbon chain group containing from 2 to 7 carbon atoms and containing 1, 2 or 3 double bond(s), preferably 1 to 4 carbon atoms and 1 double bond. Examples of such groups are are methenyl, 1-ethenyl, 2-ethenyl, 1-propenyl, 2-propenyl, 3-propenyl, isopropenyl, isobutenyl, sec-butenyl, tert-butenyl, pentenyl, and n-hexenyl as well as those specifically illustrated by the examples herein below.

"$C_1$-$C_7$-haloalkyl" denotes a $C_1$-$C_7$-alkyl group as defined above which is substituted by one or more halogen. Examples of $C_1$-$C_7$-haloalkyl include, but are not limited to, methyl, ethyl, propyl, isopropyl, isobutyl, sec-butyl, tert-butyl, pentyl and n-hexyl substituted by one or more Cl, F, Br or I atom(s) as well as those groups specifically illustrated by the examples herein below. Prefered $C_1$-$C_7$-haloalkyl are difluoro- or trifluoro-methyl or ethyl.

"$C_1$-$C_7$-alkoxy" denotes a group wherein the alkyl group is as defined above and the alkyl group is connected via an oxygen atom. Prefered alkoxy groups are MeO— (methoxy) and Et-O (ethoxy) as well as those groups specifically illustrated by the examples herein below.

"$C_1$-$C_7$-haloalkoxy" denotes a $C_1$-$C_7$-alkoxy group as defined above which is substituted by one or more halogen atom. Examples of $C_1$-$C_7$ haloalkyl include, but are not limited to, methoxy, ethoxy, propoxy, isopropoxy, and isobutoxy, substituted by one or more Cl, F, Br or I atom(s) as well as those groups specifically illustrated by the examples hereinbelow. Prefered $C_1$-$C_7$-haloalkoxy are difluoro- or trifluoromethoxy or ethoxy groups.

"Halogen" or "halo" denotes chlorine, iodine, fluorine and bromine.

"$C_1$-$C_7$-alkylsulfonyl" denotes a sulfonyl group which is substituted by a $C_1$-$C_7$-alkyl group as defined herein above. Examples of $C_1$-$C_7$-alkylsulfonyl include, but are not limited to, methylsulfphonyl and ethylsulfonyl as well as those groups specifically illustrated by the examples herein below.

"di($C_1$-$C_7$)alkylamino" denotes a —$NR^cR^d$ group, wherein $R^c$ and $R^d$ are $C_1$-$C_7$-alkyl groups as defined herein above. Examples of di($C_1$-$C_7$)alkylamino groups include, but are not limited to, di(methyl)amino, di(ethyl)amino, and methylethylamino, as well as those groups specifically illustrated by the examples herein below.

"Hydroxy or hydroxyl" denotes an —OH group.

"$C_3$-$C_8$-cycloalkyl" or "$C_5$-$C_7$-cycloalkyl" denotes a saturated carbon cyclic ring having 3 to 8 or 5 to 7 carbon atoms as ring members, respectively, and includes, but is not limited to, cyclopropyl, cyclobutyl, cyclopentyl, cyclohexyl, and cycloheptyl, as well as those groups specifically illustrated by the examples herein below.

"Heterocycloalkyl" or "Heterocycloalkyl having 3 to 8, 4 to 8 or 5 to 7 ring atoms" denote a saturated mono- or bi-cyclic ring comprising of 3 to 8, in particular 4 to 8 and more particularly 5 to 7 ring atoms and furthermore containing one, two, or three ring heteroatoms selected from N, O, or S, the remaining ring atoms being C. Preferred 3 to 8 membered heterocycloalkyl groups are 5 or 6 membered heterocycloalkyl groups. Examples include, but are not limited to, optionally substituted azetidinyl, piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiomorpholinyl, thiomorpholinylsulfoxide, thiomorpholinylsulfone, dihydroquinolinyl, dihydrisoquinolinyl, tetrahydroquinolinyl, tetrahydroisoquinolinyl, 1-oxo-thiomorpholin, 1,1-dioxo-thiomorpholin, 1,4-diazepane, and 1,4-oxazepane and 8-oxa-3-aza-bicyclo[3.2.1]oct-3-yl, as well as those groups specifically illustrated by the examples herein below.

"Heteroaryl" means a monocyclic or bicyclic radical of 5 to 12 and preferably 5 to 9 ring atoms having at least one aromatic ring and furthermore containing one, two, or three ring heteroatoms selected from N, O, or S, the remaining ring atoms being C. Heteroaryl can optionally be substituted with one, two, three or four substituents, wherein each substituent is independently hydroxy, cyano, alkyl, alkoxy, thioalkyl, halo, haloalkyl, hydroxyalkyl, alkoxycarbonyl, amino, acetyl, —$NHCOOC(CH_3)_3$ or halogen as defined above, substituted benzyl, or for the non aromatic part of cyclic ring also by oxo, unless otherwise specifically indicated. Examples of heteroaryl moieties include, but are not limited to, optionally substituted imidazolyl, optionally substituted oxazolyl, optionally substituted thiazolyl, optionally substituted pyrazinyl, optionally substituted pyrrolyl, optionally substituted pyrazinyl, optionally substituted pyridinyl, optionally substituted pyrimdinyl, optionally substituted indonyl, optionally substituted isoquinolinyl, optionally substituted carbazol-9-yl, optionally substituted furanyl, optionally substituted benzofuranyl, optionally substituted benzo[1,2,3]thiadiazolyl, optionally substituted benzo[b]thiophenyl, optionally substituted 9H-thioxanthenyl, optionally substituted thieno[2,3-c]pyridinyl and the like or those which are specifically exemplified herein.

"$R^5$ together with $R^4$ together form a ring selected from the group consisting of $C_5$-$C_7$-cycloalkyl; heterocycloalkyl having 5 to 7 ring atoms; phenyl; pyridinyl; or pyrimidinyl" denotes a $C_5$-$C_7$-cycloalkyl, heterocycloalkyl having 5 to 7 ring atoms, phenyl, pyridinyl or pyrimidinyl group as defined above which is fused to the thieno-pyridine group via $R^5$ and $R^4$. Examples of such group are, but are not limited to, cyclopentane, cyclohexane, phenyl, pyridine, tetrahydropyrane and 2,2-difluoro-[1,3]dioxolane. Said groups may be substituted by —C(O)O—$C_1$-$C_7$-alkyl group(s).

"Thiophenyl" is synonymous with "thienyl" and each represents a thiophene substituent, i.e., $C_4H_4S$.

"Pharmaceutically acceptable," such as pharmaceutically acceptable carrier, excipient, etc., means pharmacologically acceptable and substantially nontoxic to the subject to which the particular compound is administered.

The term "pharmaceutically acceptable acid addition salts" embraces salts with inorganic and organic acids, which include but are not limited to hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid.

"Therapeutically effective amount" means an amount that is effective to prevent, alleviate or ameliorate symptoms of disease or prolong the survival of the subject being treated.

The present invention provides compounds of formula I

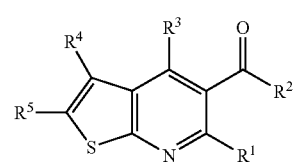

wherein $R^1$ is hydrogen, $C_1$-$C_7$-alkyl, $C_1$-$C_7$-haloalkyl, or $C_3$-$C_8$-cycloalkyl;

$R^2$ is $C_1$-$C_7$-alkyl, $C_1$-$C_7$-haloalkyl, $C_3$-$C_8$-cycloalkyl, optionally substituted aryl or optionally substituted heteroaryl having 5 to 9 ring atoms, wherein the substituents are selected from the group consisting of halo, $C_1$-$C_7$-alkoxy, $C_1$-$C_7$-haloalkyl, $C_1$-$C_7$-haloalkoxy, $C_1$-$C_7$-alkylsulfonyl, and —C(O)O—$C_1$-$C_7$-alkyl;

$R^3$ is —$NR^aR^b$; optionally substituted heterocycloalkyl having 3 to 8 ring atoms; optionally substituted aryl or optionally substituted heteroaryl having 5 to 9 ring atoms, wherein the substituents are selected from the group consisting of halo, $C_1$-$C_7$-alkoxy, $C_1$-$C_7$-haloalkyl, $C_1$-$C_7$-haloalkoxy, $C_1$-$C_7$-alkylsulfonyl, and —C(O)O—$C_1$-$C_7$-alkyl;

$R^4$ is hydrogen or $C_1$-$C_7$-alkyl; and $R^5$ is hydrogen, halo, $C_1$-$C_7$-alkyl, $C_2$-$C_7$-alkenyl, —$NR^aR^b$; optionally substituted aryl or optionally substituted heteroaryl having 5 to 9 ring atoms, wherein the substituents are selected from the group consisting of halo, cyano, $C_1$-$C_7$-alkyl, $C_1$-$C_7$-haloalkyl, $C_1$-$C_7$-alkoxy, $C_1$-$C_7$-haloalkoxy, $C_1$-$C_7$-alkylsulfonyl, and —C(O)O—$C_1$-$C_7$-alkyl;

or $R^5$ together with $R^4$ forms a ring selected from the group consisting of $C_5$-$C_7$-cycloalkyl, heterocycloalkyl having 5 to 7 ring atoms, phenyl, pyridinyl, and pyrimidinyl each of which are optionally substituted or by one or more halo, cyano, $C_1$-$C_7$-alkylsulfonyl, $C_1$-$C_7$-alkyl, $C_1$-$C_7$-haloalkyl, $C_1$-$C_7$-alkoxy, $C_1$-$C_7$-haloalkoxy, or —C(O)O—$C_1$-$C_7$-alkyl;

$R^a$ and $R^b$ are each independently $C_1$-$C_7$-alkyl, or $R^a$ and $R^b$, together with the nitrogen atom to which they are attached, form an heterocycloalkyl group having 3 to 8 ring atoms which is optionally substituted by one or more halo, $C_1$-$C_7$-alkyl, $C_1$-$C_7$-alkoxy, hydroxy, phenyl or di($C_1$-$C_7$)alkylamino;

and a pharmaceutically acceptable salt thereof.

Encompassed by formula I are the following compounds of formula Ia

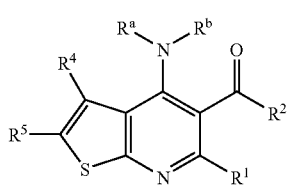

(Ia)

wherein $R^1$, $R^2$, $R^4$, $R^5$, $R^a$ and $R^b$ are as defined hereinbefore for the compounds of formula I. In fact, compounds of formula Ia are those compounds of formula I wherein $R^3$ is $NR^aR^b$.

Also encompassed by formula I are the following compounds of formula Ib

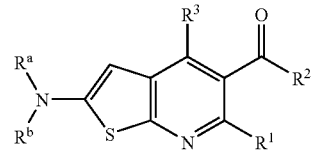

(Ib)

wherein $R^1$, $R^2$, $R^3$, $R^a$ and $R^b$ are as defined hereinbefore for the compounds of formula I. In fact, compounds of formula Ib are those compounds of formula I wherein $R^4$ is H and $R^5$ is $NR^aR^b$.

Also encompassed by formula I are the following compounds of formula Ic

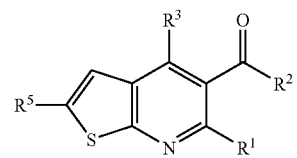

(Ic)

wherein $R^1$, $R^2$, and $R^3$ are as defined hereinbefore for the compounds of formula I and $R^5$ is selected from the group consisting of $C_2$-$C_7$-alkenyl and optionally substituted aryl or heteroaryl having 5 to 9 ring atoms, wherein the substituents are selected from the group consisting of halo, cyano, $C_1$-$C_7$-alkyl, $C_1$-$C_7$-haloalkyl, $C_1$-$C_7$-alkoxy, $C_1$-$C_7$-haloalkoxy, $C_1$-$C_7$-alkylsulfonyl, and —C(O)O—$C_1$-$C_7$-alkyl. In fact, compounds of formula Ic are those compounds of formula I wherein $R^4$ is H and $R^5$ is selected from the group consisting of $C_2$-$C_7$-alkenyl and optionally substituted aryl or heteroaryl having 5 to 9 ring atoms, wherein the substituents are selected from the group consisting of halo, cyano, $C_1$-$C_7$-alkyl, $C_1$-$C_7$-haloalkyl, $C_1$-$C_7$-alkoxy, $C_1$-$C_7$-haloalkoxy, $C_1$-$C_7$-alkylsulfonyl, and —C(O)O—$C_1$-$C_7$-alkyl.

For the compounds of formula I, Ia, Ib and Ic the following groups are preferred: preferred groups for $R^1$ are selected from the group consisting of methyl, ethyl, propyl, i-propyl, butyl, i-butyl, and t-butyl.

Preferred groups for $R^2$ are selected from the group consisting of methyl, ethyl, propyl, i-propyl, butyl, i-butyl, t-butyl, cyclopropyl, cyclobutyl, cyclopentyl, cyclohexyl, phenyl, $CHF_2$ and $CF_3$.

Preferred groups for $R^3$ are selected from the group consisting of:

phenyl optionally substituted by one or more halo, preferably chloro or fluoro, $C_1$-$C_7$-alkoxy, preferably methoxy; $C_1$-$C_7$-alkylsulfonyl, preferably methylsulfonyl, or —C(O)O—$C_1$-$C_7$-alkyl, preferably C(O)—O—$CH_3$;

thiophenyl, preferably, thiophen-2-yl;

furanyl, preferably furan-2-yl;

piperidine, preferably, piperidin-1-yl; and morpholine.

Preferred groups for $R^4$ are selected from the group consisting of:
hydrogen and
$C_1$-$C_7$-alkyl, preferably methyl.

Preferred groups for $R^5$ are selected from the group consisting of:
$C_1$-$C_7$-alkyl, preferably methyl;
Aryl, preferably phenyl;
Halo, preferably chloro; and
Hydrogen.

Preferred groups for $R^5$ together with $R^4$ when they form a ring are selected from the group consisting of:
$C_5$-$C_7$-cycloalkyl, preferably cyclopentyl, cyclohexyl, and cycloheptyl;
aryl, preferably phenyl;
heteroaryl having 5 to 9 ring atoms, preferably pyridinyl or pyrimidinyl;
heterocycloalkyl having 5 to 7 ring atoms, preferably tetrahydrofurane, or piperidinyl optionally substituted by —C(O)O—$C_1$-$C_7$-alkyl.

Preferred compounds of the invention are those compounds of formula I, wherein
$R^1$ is $C_1$-$C_7$-alkyl, preferably methyl;
$R^2$ is $C_1$-$C_7$-alkyl, preferably methyl; $C_1$-$C_7$-haloalkyl, preferably $CF_3$; or $C_3$-$C_8$-cycloalkyl, preferably cyclopropyl;
$R^3$ is heterocycloalkyl having 3 to 8 ring atoms, preferably piperidin; aryl, preferably phenyl;
or heteroaryl having 5 to 9 ring atoms, preferably furanyl or thiophenyl, which are optionally substituted by one or more substituent(s) selected from the group consisting of halo, preferably chloro or fluoro; $C_1$-$C_7$-alkoxy, preferably methoxy; $C_1$-$C_7$-alkylsulfonyl, preferably methylsulfonyl; and —C(O)O—$C_1$-$C_7$-alkyl, preferably C(O)O-Me;
$R^4$ is hydrogen or $C_1$-$C_7$-alkyl, preferably methyl;
$R^5$ is hydrogen; halo, preferably chloro; $C_1$-$C_7$-alkyl, preferably methyl; or aryl, preferably phenyl;
or $R^5$ together with $R^4$ forms a ring selected from the group consisting of $C_5$-$C_7$-cycloalkyl; heterocycloalkyl having 5 to 7 ring atoms; phenyl; pyridinyl; or pyrimidinyl which are optionally substituted or by one or more halo, cyano, $C_1$-$C_7$-alkylsulfonyl, $C_1$-$C_7$-alkyl, $C_1$-$C_7$-haloalkyl, $C_1$-$C_7$-alkoxy, $C_1$-$C_7$-haloalkoxy, and —C(O)O—$C_1$-$C_7$-alkyl, as well a pharmaceutically acceptable salts thereof.

Also preferred compounds of the invention are those compounds of formula I wherein $R^2$ is $C_1$-$C_7$-alkyl, for example the following compounds:
1-(2-Methyl-4-phenyl-6,7-dihydro-5H-cyclopenta[4,5]thieno[2,3-b]pyridin-3-yl)-ethanone;
1-(2-Methyl-4-thiophen-2-yl-6,7-dihydro-5H-cyclopenta[4,5]thieno[2,3-b]pyridin-3-yl)-ethanone;
1-(2-Methyl-4-thiophen-2-yl-5,6,7,8-tetrahydro-benzo[4,5]thieno[2,3-b]pyridin-3-yl)-ethanone;
1-[4-(4-Methoxy-phenyl)-2-methyl-5,6,7,8-tetrahydro-benzo[4,5]thieno[2,3-b]pyridin-3-yl]-ethanone;
1-(2-methyl-4-phenyl-benzo[4,5]thieno[2,3-b]pyridin-3-yl)-ethanone;
1-[4-(4-Methanesulfonyl-phenyl)-2-methyl-6,7-dihydro-5H-cyclopenta[4,5]thieno[2,3-b]pyridin-3-yl]-ethanone;
1-(2,3,6-Trimethyl-4-phenyl-thieno[2,3-b]pyridin-5-yl)-ethanone;
1-(4-Furan-2-yl-2-methyl-6,7-dihydro-5H-cyclopenta[4,5]thieno[2,3-b]pyridin-3-yl)-ethanone;
1-(2-Methyl-4-phenyl-9-thia-1,7-diaza-fluoren-3-yl)-ethanone;
3-Acetyl-2-methyl-4-phenyl-5,8-dihydro-6H-9-thia-1,7-diaza-fluorene-7-carboxylic acid methyl ester; and
1-(6-Methyl-2,4-diphenyl-thieno[2,3-b]pyridin-5-yl)-ethanone.

Other preferred are those compounds of formula I wherein, wherein $R^2$ is $C_1$-$C_7$-haloalkyl, for example the following compounds:
1-[4-(3,4-Dichloro-phenyl)-2-methyl-6,7-dihydro-H-cyclopenta[4,5]thieno[2,3-b]pyridin-3-yl]-2,2,2-trifluoro-ethanone;
2,2,2-Trifluoro-1-(2-methyl-4-thiophen-2-yl-6,7-dihydro-5H-cyclopenta[4,5]thieno[2,3-b]pyridin-3-yl)-ethanone;
2,2,2-Trifluoro-1-(2-methyl-4-phenyl-6,7-dihydro-5H-cyclopenta[4,5]thieno[2,3-b]pyridin-3-yl)-ethanone;
2,2,2-Trifluoro-1-(2-methyl-4-thiophen-2-yl-5,6,7,8-tetrahydro-benzo[4,5]thieno[2,3-b]pyridin-3-yl)-ethanone;
2,2,2-Trifluoro-1-[4-(4-methoxy-phenyl)-2-methyl-5,6,7,8-tetrahydro-benzo[4,5]thieno[2,3-b]pyridin-3-yl]-ethanone;
2,2,2-Trifluoro-1-[4-(4-methoxy-phenyl)-2-methyl-6,7-dihydro-5H-cyclopenta[4,5]thieno[2,3-b]pyridin-3-yl)-ethanone;
2,2,2-Trifluoro-1-(2-methyl-4-phenyl-benzo[4,5[thieno[2,3-b]pyridin-3-yl)-ethanone;
2,2,2-Trifluoro-1-[4-(4-methanesulfonyl-phenyl)-2-methyl-6,7-dihydro-5H-cyclopenta[4,5[thieno[2,3-b]pyridin-3-yl)-ethanone;
2,2,2-Trifluoro-1-(2,3,6-trimethyl-4-phenyl-thieno[2,3-b]pyridin-5-yl)-ethanone;
2,2,2-Trifluoro-1-[4-(4-fluoro-phenyl)-2-methyl-6,7-dihydro-5H-cyclopenta[4,5]thieno[2,3-b]pyridin-3-yl]-ethanone;
2,2,2-Trifluoro-1-(4-furan-2-yl-2-methyl-6,7-dihydro-5H-cyclopenta[4,5]thieno[2,3-b]pyridin-3-yl)-ethanone;
2,2,2-Trifluoro-1-(6-methyl-4-phenyl-thieno[2,3-b]pyridin-5-yl)-ethanone;
1-(2-Chloro-6-methyl-4-phenyl-thieno[2,3-b]pyridin-5-yl)-2,2,2-trifluoro-ethanone;
2,2,2-Trifluoro-1-[4-(4-fluoro-phenyl)-6-methyl-thieno[2,3-b]pyridin-5-yl]-ethanone; and
1-[2-Chloro-4-(4-fluoro-phenyl)-6-methyl-thieno[2,3-b]pyridin-5-yl]-2,2,2-trifluoro-ethanone.

Still other preferred compounds of the invention are those compounds of formula I, wherein $R^2$ is $C_3$-$C_8$-cycloalkyl, for example the following compounds:
Cyclopropyl-(2-methyl-4-phenyl-6,7-dihydro-5H-cyclopenta[4,5]thieno[2,3-b]pyridin-3-yl)-methanone;
Cyclopropyl-(6-methyl-4-phenyl-thieno[2,3-b]pyridin-5-yl)-methanone;
Cyclopropyl-(2-methyl-4-thiophen-2-yl-6,7-dihydro-5H-cyclopenta[4,5]thieno[2,3-b]pyridin-3-yl)-methanone;
Cyclopropyl-(4-furan-2-yl-2-methyl-6,7-dihydro-5H-cyclopenta[4,5]thieno[2,3-b]pyridin-3-yl)-methanone;
Cyclopropyl-[(4-(3,4-dichloro-phenyl)-2-methyl-6,7-dihydro-5H-cyclopenta [4,5]thieno[2,3-b]pyridin-3-yl)-methanone;
Cyclopropyl-[(4-(3,4-dichloro-phenyl)-2-methyl-5,6,7,8-tetrahydro-benzo[4,5]thieno[2,3-b]pyridin-3-yl)]-methanone;
Cyclopropyl-[4-(4-methoxy-phenyl)-2-methyl-6,7-dihydro-5H-cyclopenta [4,5]thieno[2,3-b]pyridin-3-yl)]-methanone;
Cyclopropyl-[4-(4-methoxy-phenyl)-2-methyl-5,6,7,8-tetrahydro-benzo[4,5]thieno[2,3-b]pyridin-3-yl)]-methanone;
4-(3-Cyclopropanecarbonyl-2-methyl-6,7-dihydro-5H-cyclopenta[4,5]thieno[2,3-b]pyridin-4-yl)-benzoic acid methyl ester;

4-(3-Cyclopropanecarbonyl-2-methyl-5,6,7,8-tetrahydro-benzo[4,5]thieno[2,3-b]pyridin-4-yl)-benzoic acid methyl ester;

4-(3-Cyclopropanecarbonyl-2-methyl-6,7,8,9-tetrahydro-5H-10-thia-1-aza-benzo[a]azulen-4-yl)-benzoic acid methyl ester;

Cyclopropyl-[4-(3,4-dichloro-phenyl)-2-methyl-6,7,8,9-tetrahydro-5H-1-thia-1-aza-benzo [a]azulen-3-yl)-methanone;

Cyclopropyl-(2-methyl-4-phenyl-9-thia-1,7-diaza-fluoren-3-yl)-methanone;

Cyclopropyl-(2-methyl-4-phenyl-5,8-dihydro-6H-7-oxa-9-thia-1-aza-fluoren-3-yl)-methanone;

Cyclopropyl-(6-methyl-4-piperidin-1-yl-2,3-dihydro-1H-8-thia-7-aza-cyclopenta[a]inden-5-yl)-methanone; and Cyclopropyl-(6-Methyl-2,4-diphenyl-thieno[2,3-b]pyridin-5-yl)-methanone.

The afore-mentioned compounds of formula I wherein $R^3$ is optionally substituted aryl or heteroaryl having 5 to 9 ring atoms as defined hereinbefore can be manufactured by the following process of the invention comprising the step of reacting a compound of formula IV:

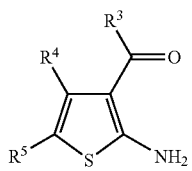

IV with a compound of formula V:

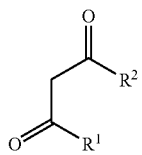

V to obtain the compound of formula I, wherein $R^1$, $R^2$, $R^3$, $R^4$, and $R^5$ are as defined hereinbefore, and if desired, converting the compound of formula I obtained into a pharmaceutically acceptable acid addition salt. This process of manufacture is further detailed in scheme 1 hereinafter.

The afore-mentioned compounds of formula Ia can be manufactured in accordance with the invention by the following process comprising the step of reacting a compound of formula VI with a compound of formula VII:

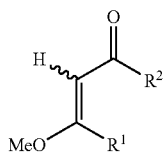

VII in order to obtain a compound of formula VIII:

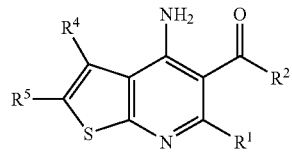

VIII and subsequently alkylating the compound of formula VIII in order to obtain the compound of formula Ia, wherein $R^1$, $R^2$, $R^4$, $R^5$, $R^a$ and $R^b$ are as defined hereinbefore for the compounds of formula I;

and if desired, converting the compound of formula Ia obtained into a pharmaceutically acceptable acid addition salt. This process of manufacture is further detailed in scheme 2 hereinafter.

The afore-mentioned compounds of formula Ib can be manufactured in accordance with the invention by the following process comprising the step of reacting a compound of formula XI:

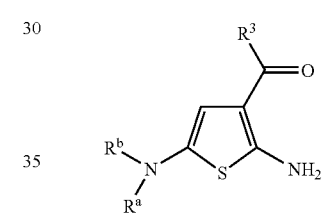

XI with a compound of formula V:

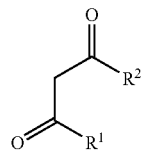

V in order to obtain the compound of formula Ib, wherein $R^1$, $R^2$, $R^3$, $R^a$ and $R^b$ are as defined hereinbefore for the compounds of formula I;

and if desired, converting the compound of formula Ia obtained into a pharmaceutically acceptable acid addition salt. This process of manufacture is further detailed in scheme 3 hereinafter.

The afore-mentioned compounds of formula Ic can be manufactured in accordance with the invention by the following process comprising the step of:

reacting a compound of formula X:

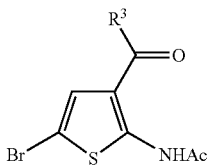

with a compound of formula XII:

$R^5$—B(OH)$_2$    (XII)

so as to obtain a compound of formula XIII:

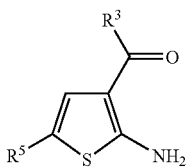    XIII and reacting the compound of formula XIII with a compound of formula V:

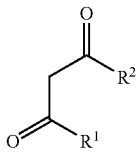    V in order to obtain the compound of formula Ic, wherein $R^1$, $R^2$, $R^3$, are as defined hereinbefore for the compounds of formula I, $R^4$ is H and $R^5$ is selected from the group consisting of $C_2$-$C_7$-alkenyl and optionally substituted aryl or heteroaryl having 5 to 9 ring atoms, wherein the substituents are selected from the group consisting of halo, cyano, $C_1$-$C_7$-alkyl, $C_1$-$C_7$-haloalkyl, $C_1$-$C_7$-alkoxy, $C_1$-$C_7$-haloalkoxy, $C_1$-$C_7$-alkylsulfonyl, and —C(O)O—$C_1$-$C_7$-alkyl; and if desired, converting the compound of formula Ic obtained into a pharmaceutically acceptable acid addition salt. This process of manufacture is further detailed in scheme 4 hereinafter.

The invention also encompasses a compound of formulae I, Ia, Ib and Ic whenever it is prepared according to the above-mentioned processes.

The following general schemes 1 to 3 further illustrate certain embodiments of the preparation of the compounds according to the invention. In these schemes, and unless otherwise stated, all starting materials, building blocks and intermediates are commercially available.

In certain embodiments, the compounds of formula I wherein $R^3$ is optionally substituted aryl- or heteroaryl having 5 to 9 ring atoms can be prepared according to the general method of scheme 1:

Scheme 1:

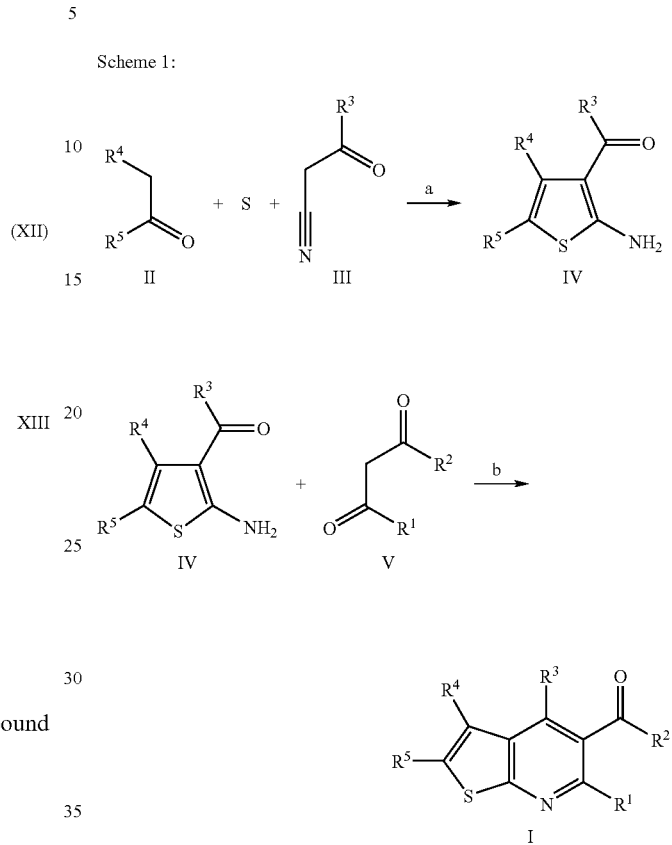

a) Morpholine 1 eq., EtOH, reflux; b) H$_2$SO$_4$ cat., AcOH

The formation of 2-amino-thiophene derivatives of formula IV is achieved from the base-catalyzed (morpholine) condensation of an enolisable carbonyl compound II with a methylene active nitrile III and sulfur by the Gewald reaction (K. Gewald, E. Schinke, H. Böettcher; *Chem. Ber.* 1966, 99, 94-100). Novel thieno pyridine derivatives of formula I were obtained following a Friedlander type reaction (P. Friedlander, *Berichte,* 1882, 15, 2572) between the 2-aminothiophene IV and a 1,3-dione V in an acid (e.g. acetic acid) and a catalyst (e.g. a catalytic amount of sulfuric acid) (A. Arcadi, M. Chiarini, S. Giuseppe, F. Marinelli, *Synlett,* 2003, 2, 203 and references therein).

In certain embodiments, the compounds of formula I wherein $R^3$ is NR$^a$R$^b$ are herein designated as compounds Ia and can be prepared according to the general method described in scheme 2 hereinbelow:

Scheme 2:

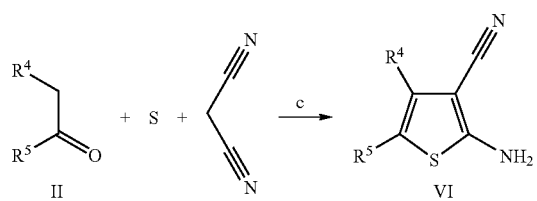

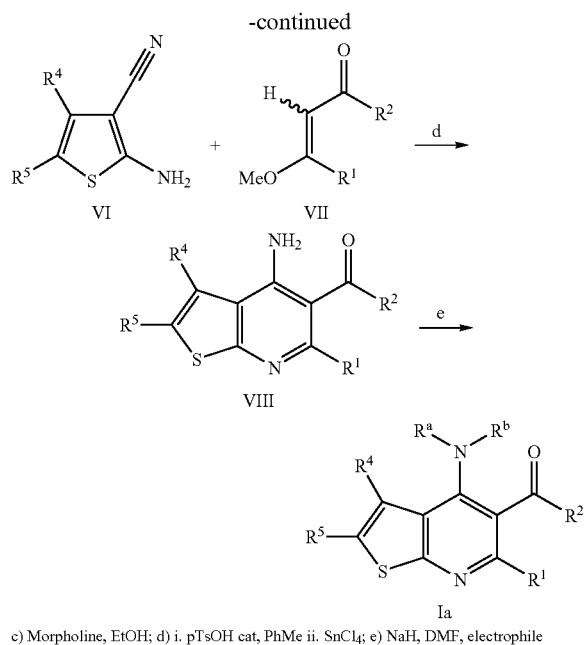

c) Morpholine, EtOH; d) i. pTsOH cat, PhMe ii. SnCl₄; e) NaH, DMF, electrophile

The formation of 2-amino,3-CN-thiophene derivatives VI are either known or can be prepared using procedures similar to the Gewald reaction described in scheme 1 by reacting malonitrile and sulfur with the appropriate ketone of formula II. (K. Gewald, E. Schinke, H. Böettcher, *Chem. Ber.* 1966, 99, 94-100). Novel 4-amino thieno[2,3-b]pyridine derivatives VIII were prepared using a procedure reported in WO93/13104, by a condensation step between compounds of formula VI and VII, followed without isolation of the intermediate by a cyclisation step with a Lewis acid. Final derivatives Ia were obtained by conventional procedures for the alkylation of a primary amine.

In certain embodiments, the compounds of formula I wherein $R^1$, $R^2$, and $R^3$ are as defined hereinabove for formula I, $R^4$ is H and $R^5$ is —$NR^aR^b$, herein designated as compounds Ib, can be prepared according to the general method described in scheme 3 hereinbelow:

Scheme 3:

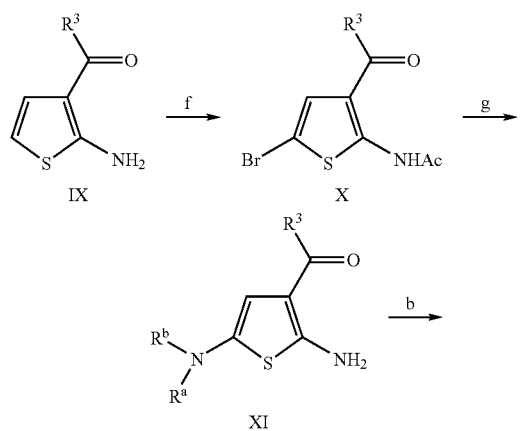

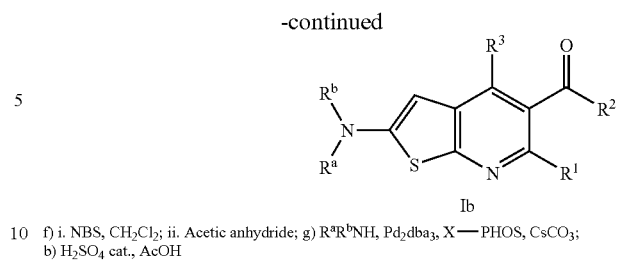

f) i. NBS, CH₂Cl₂; ii. Acetic anhydride; g) $R^aR^bNH$, Pd₂dba₃, X—PHOS, CsCO₃; b) H₂SO₄ cat., AcOH 2-Amino thiophenes IX (commercially available or described in literature) are brominated in the 4-position with N-bromo succinimide in CH₂Cl₂ followed by the immediate addition of acetic anhydride to afford derivatives X. Following a methodology developed by S. L. Buchwald et al. (*J. Org. Chem.* 2000, 65, 1144) novel derivatives XI were obtained, which undergo a Friedlander type reaction with compound of formula V (see scheme 1) to yield compounds of formula Ib.

In certain embodiments, the compounds of formula I wherein $R^1$, $R^2$, and $R^3$ are as defined hereinabove for formula I, $R^4$ is H and $R^5$ is selected from the group consisting of $C_2$-$C_7$-alkenyl and optionally substituted aryl or heteroaryl having 5 to 9 ring atoms, wherein the substituents are selected from the group consisting of halo, cyano, $C_1$-$C_7$-alkyl, $C_1$-$C_7$-haloalkyl, $C_1$-$C_7$-alkoxy, $C_1$-$C_7$-haloalkoxy, $C_1$-$C_7$-alkylsulfonyl, or —C(O)O—$C_1$-$C_7$-alkyl, herein designated as compounds Ic, can be prepared according to the general method described in scheme 4 hereinbelow:

Scheme 4:

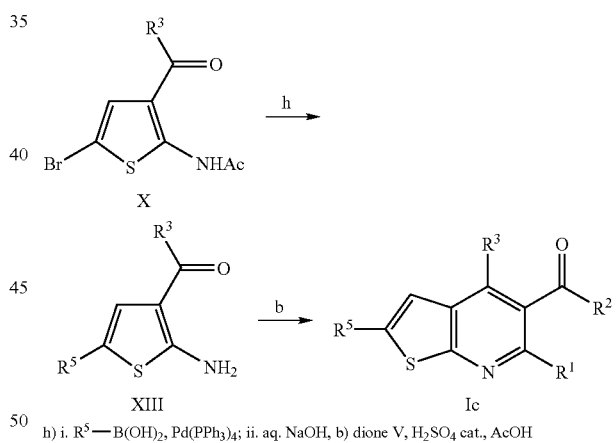

h) i. $R^5$—B(OH)₂, Pd(PPh₃)₄; ii. aq. NaOH, b) dione V, H₂SO₄ cat., AcOH

Following a Suzuki methodology, by coupling a bromothiophene intermediate X (described in scheme 3) with a commercially available boronic acid of formula $R^5$—B(OH)₂ (XII), derivatives XIII were obtained after deprotection of the acetamide under basic conditions. These derivatives XIII undergo a Friedlander type reaction with compound of formula V (see scheme 1) to yield compounds of formula Ic.

The preparation of compounds of formulae I, Ia, Ib and Ic are further described in detail in working examples 1-40.

As mentioned earlier, the compounds of formula I and their pharmaceutically acceptable addition salts possess valuable pharmacological properties. It has been found that the compounds of the present invention have an affinity to the $GABA_B$ receptor.

The compounds were investigated in accordance with the tests given hereinafter.

Intracellular $Ca^{2+}$ Mobilization Assay

The Chinese Hamster Ovary (CHO) cells stably expressing human $GABA_BR1aR2a$ and $G\alpha16$ were seeded at $5\times10^4$ cells/well in the poly-D-lysine treated, 96-well, black/clear-bottomed plates (BD Biosciences, Palo Alto, Calif.). 24 h later, the cells were loaded for 90 min at 37° C. with 4 µM Flou-4 acetoxymethyl ester (Catalog No. F-14202, Molecular Probes, Eugene, Oreg.) in loading buffer (1×HBSS, 20 mM HEPES, 2.5 mM Probenecid). Hanks' Balanced Salt Solution (HBSS) (10×) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with loading buffer to remove excess dye and intracellular calcium mobilization, $[Ca^{2+}]_i$ were measured using a Fluorometric Imaging Plate Reader (FLIPR, Molecular Devices, Menlo Park, Calif.) as described previously (Porter et al., Br. J. Pharmacol., 128, 13-20, 1999). The enhancers were applied 15 min before the application of the GABA. For GABA shift assay, concentration-response curves of GABA (0.0003-30 µM) were determined in the absence and presence of 10 µM enhancer. The GABA-shift is defined as Log [$EC_{50}$ (GABA+10 µM enhancer)/$EC_{50}$ (GABA alone)]. The % maximum enhancing effect (% $E_{max}$) and potency ($EC_{50}$ value) of each enhancer was determined from concentration-response curve of the enhancer (0.001-30 µM) in the presence of 10 nM GABA ($EC_{10}$). Responses were measured as peak increase in fluorescence minus basal, normalized to the maximal stimulatory effect induced by 10 µM GABA alone (considered 100%) and 10 nM GABA alone (considered 0%). The data were fitted with the equation $Y=100+(Max-100)/(1+(EC_{50}/[drug])^n)$ where Max is the maximum effect, $EC_{50}$ the concentration eliciting a half-maximum effect and n the Hill slope.

| | Intracellular $Ca^{2+}$ mobilization Assay in CHO-$GABA_BR1aR2a$-$G\alpha16$ cell | | |
|---|---|---|---|
| Example | $E_{max}$ (%) at 10 nM GABA alone = 0% 10 µM GABA alone = 100% | $EC_{50}$ (µM) at 10 nM GABA | GABA shift Log [$EC_{50}$(GABA + 10 µM cp)/ $EC_{50}$(GABA alone)] |
| 1 | 47 | 14.7 | −0.3 |
| 2 | 59 | 1.3 | −0.9 |
| 16 | 69 | 2.4 | −0.9 |
| 18 | 58 | 0.86 | −1 |
| 21 | 66 | 1.9 | −1.1 |
| 23 | 35 | 1.3 | −0.6 |
| 35 | 56 | 1.2 | −0.91 |
| 38 | 20 | 1.4 | −0.3 |

The present invention also provides pharmaceutical compositions containing compounds of the invention or pharmaceutically acceptable salts thereof and a pharmaceutically acceptable carrier. Such pharmaceutical compositions can be in the form of tablets, coated tablets, dragées, hard and soft gelatine capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semisolid and liquid polyols and the like; depending on the nature of the active substance no carriers are, however, usually required in the case of soft gelatine capsules. Suitable carriers for the production of solutions and syrups are, for example, water, polyols, sucrose, invert sugar, glucose and the like. Adjuvants, such as alcohols, polyols, glycerol, vegetable oils and the like, can be used for aqueous injection solutions of water-soluble salts of compounds of the invention, but as a rule are not necessary. Suitable carriers for suppositories are, for example, natural or hardened oils, waxes, fats, semi-liquid or liquid polyols and the like.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatine capsules, solutions, emulsions, or suspensions. The pharmaceutical compositions also can be administered rectally, for example, in the form of suppositories, or parenterally, for example, in the form of injection solutions.

Compounds of the invention areactive on the $GABA_B$ receptor. The present invention provides a method for the treatment of a disorder selected from the group consisting of anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders and gastrointestinal disorders which comprises administering to an individual a therapeutically effective amount of a compound of formula I or a pharmaceutically acceptable salt thereof. In particular, the present invention provides a method for the treatment of schizophrenia which comprises administering to an individual a therapeutically effective amount of a compound of formula I or a pharmaceutically acceptable salt thereof. The invention further provides a method for the treatment of multiples sclerosis which comprises administering to an individual a therapeutically effective amount of a compound of formula I or a pharmaceutically acceptable salt thereof. Further, the invention provides a method for treating depression which comprises administering to an individual a therapeutically effective amount of a compound of formula I or a pharmaceutically acceptable salt thereof.

The dosage can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

Mix items 1, 2 and 3 in a suitable mixer for 30 minutes.
Add items 4 and 5 and mix for 3 minutes.
Fill into a suitable capsule.

EXAMPLES

In the following examples, all the starting materials are commercially available.

Example 1

1-[4-(3,4-Dichloro-phenyl)-2-methyl-6,7-dihydro-5H-cyclopenta[4,5]thieno[2,3-b]pyridin-3-yl]-2,2,2-trifluoro-ethanone (2-Amino-5,6-dihydro-4H-cyclopenta[b]thiophen-3-yl)-(3,4-dichloro-phenyl)-methanone To a stirred solution of 0.30 g (1.40 mmol) 3-(3,4-dichloro-phenyl)-3-oxo-propionitrile in 10 ml ethanol was added 0.12 ml (1.40 mmol) cyclopentanone, 43 mg (1.40 mmol) sulfur, and 0.12 ml (1.40 mmol) morpholine. The mixture was heated at 40° C. for 48 h and then poured onto water and extracted three times with ethyl acetate. The combined organic phases were dried over sodium sulfate and concentrated in vacuo. Trituration in ether afforded 0.449 g (89%) (2-amino-5,6-dihydro-4H-cyclopenta[b]thiophen-3-yl)-(3,4-dichloro-phenyl)-methanone as a brown solid.
ES-MS m/e: 312 (%) (M+H$^+$, 100).

1-[4-(3,4-Dichloro-phenyl)-2-methyl-6,7-dihydro-5H-cyclopenta[4,5]thieno[2,3-b]pyridin-3-yl]-2,2,2-trifluoro-ethanone To a stirred solution of 50 mg (0.16 mmol) (2-amino-5,6-dihydro-4H-cyclopenta[b]thiophen-3-yl)-(3,4-dichloro-phenyl)-methanone in 2 ml acetic acid was added 0.020 ml (0.17 mmol) of 1,1,1-trifluoro-pentane-2,4-dione and one drop of sulfuric acid. The mixture was then stirred at 100° C. for 10 minutes in a microwave and then concentrated in vacuo. Flash chromatography (heptane/ethyl acetate 10:1) afforded 9 mg (14%) 1-[4-(3,4-dichloro-phenyl)-2-methyl-6,7-dihydro-5H-cyclopenta[4,5]thieno[2,3-b]pyridin-3-yl]-2,2,2-trifluoro-ethanone as a yellow solid. ES-MS m/e (%): 430 (M+H$^+$, 100).

Example 2

2,2,2-Trifluoro-1-(2-methyl-4-thiophen-2-yl-6,7-dihydro-5H-cyclopenta[4,5]thieno[2,3-b]pyridin-3-yl)-ethanone (2-Amino-5,6-dihydro-4H-cyclopenta[b]thiophen-3-yl)-thiophen-2-yl-methanone To a stirred solution of 0.30 g (1.98 mmol) 3-oxo-3-thiophenyl-2-yl-propionitrile in 10 ml ethanol was added 0.16 ml (1.98 mmol) cyclopentanone, 63 mg (1.98 mmol) sulfur, and 0.17 ml (1.98 mmol) morpholine. The mixture was heated at 90° C. for 2 h and then poured onto water and extracted three times with ethyl acetate. The combined organic phases were dried over sodium sulfate and concentrated in vacuo. Trituration in ether afforded 0.47 g (96%) (2-amino-5,6-dihydro-4H-cyclopenta[b]thiophen-3-yl)-thiophen-2-yl-methanone as a brown solid. ES-MS m/e (%): 250 (M+H$^+$, 100).

2,2,2-Trifluoro-1-(2-methyl-4-thiophen-2-yl-6,7-dihydro-5H-cyclopenta[4,5]thieno[2,3-b]pyridin-3-yl)-ethanone To a stirred solution of 59 mg (0.24 mmol) (2-amino-5,6-dihydro-4H-cyclopenta[b]thiophen-3-yl)-thiophen-2-yl-methanone in 2 ml acetic acid was added 0.038 ml (0.24 mmol) of 1,1,1-trifluoro-pentane-2,4-dione and one drop of sulfuric acid. The mixture was then stirred at 100° C. for 10 minutes in a microwave and then concentrated in vacuo. Flash chromatography (heptane/ethyl acetate 20:1) afforded 19 mg (22%) 2,2,2-trifluoro-1-(2-methyl-4-thiophen-2-yl-6,7-dihydro-5H-cyclopenta[4,5]thieno [2,3-b]pyridin-3-yl)-ethanone as a colorless oil. ES-MS m/e (%): 368 (M+H$^+$, 100).

Example 3

2,2,2-Trifluoro-1-(2-methyl-4-phenyl-6,7-dihydro-5H-cyclopenta[4,5]thieno[2,3-b]pyridin-3-yl)-ethanone (2-Amino-5,6-dihydro-4H-cyclopenta[b]thiophen-3-yl)-phenyl-methanone To a stirred solution of 0.30 g (2.06 mmol) 3-oxo-3-phenyl-propionitrile in 10 ml ethanol was added 0.18 ml (2.06 mmol) cyclopentanone, 66 mg (2.06 mmol) sulfur, and 0.18 ml (2.06 mmol) morpholine. The mixture was heated at 90° C. for 2 h and then poured onto water and extracted three times with ethyl acetate. The combined organic phases were dried over sodium sulfate and concentrated in vacuo. Trituration in ether afforded 0.50 g (98%) (2-amino-5,6-dihydro-4H-cyclopenta[b]thiophen-3-yl)-phenyl-methanone as a brown solid. ES-MS m/e (%): 244 (M+H+, 100).

2,2,2-Trifluoro-1-(2-methyl-4-phenyl-6,7-dihydro-5H-cyclopenta[4,5]thieno[2,3-b]pyridin-3-yl)-ethanone To a stirred solution of 50 mg (0.20 mmol) (2-amino-5,6-dihydro-4H-cyclopenta[b]thiophen-3-yl)-phenyl-methanone (the preparation of which is described in example 2) in 2 ml acetic acid was added 0.026 ml (0.20 mmol) of 1,1,1-trifluoro-pentane-2,4-dione and one drop of sulfuric acid. The mixture was then stirred at 100° C. for 10 minutes in a microwave and then concentrated in vacuo. Flash chromatography (heptane/ethyl acetate 20:1) afforded 20 mg (27%) 2,2,2-trifluoro-1-(2-methyl-4-phenyl-6,7-dihydro-5H-cyclopenta[4,5]thieno [2,3-b]pyridin-3-yl)-ethanone as an orange oil. ES-MS m/e (%): 362 (M+H+, 100).

Example 4

1-(2-Methyl-4-phenyl-6,7-dihydro-5H-cyclopenta[4,5]thieno[2,3-b]pyridin-3-yl)-ethanone To a stirred solution of 56 mg (0.23 mmol) (2-amino-5,6-dihydro-4H-cyclopenta[b]thiophen-3-yl)-phenyl-methanone in 2 ml acetic acid was added 0.016 ml (0.24 mmol) of pentane-2,4-dione and one drop of sulfuric acid. The mixture was then stirred at 100° C. for 10 minutes in a microwave and then concentrated in vacuo. Flash chromatography (heptane/ethyl acetate 6:1) afforded 33 mg (47%) 1-(2-methyl-4-phenyl-6,7-dihydro-5H-cyclopenta[4,5]thieno [2,3-b]pyridin-3-yl)-ethanone as a yellow solid. ES-MS m/e (%): 308 (M+H+, 100).

Example 5

1-(2-Methyl-4-thiophen-2-yl-6,7-dihydro-5H-cyclopenta[4,5]thieno[2,3-b]pyridin-3-yl)-ethanone To a stirred solution of 55 mg (0.22 mmol) (2-amino-5,6-dihydro-4H-cyclopenta[b]thiophen-3-yl)-thiophen-2-yl-methanone in 2 ml acetic acid was added 0.016 ml (0.24 mmol) of pentane-2,4-dione and one drop of sulfuric acid. The mixture was then stirred at 80° C. for 15 minutes in a microwave and then concentrated in vacuo. Flash chromatography (heptane/ethyl acetate 6:1) afforded 27 mg (39%) 1-(2-methyl-4-thiophen-2-yl-6,7-dihydro-5H-cyclopenta[4,5]thieno [2,3-b]pyridin-3-yl)-ethanone as a yellow solid. ES-MS m/e (%): 314 (M+H+, 100).

Example 6

2,2,2-Trifluoro-1-(2-methyl-4-thiophen-2-yl-5,6,7,8-tetrahydro-benzo[4,5]thieno[2,3-b]pyridin-3-yl)-ethanone (2-Amino-4,5,6,7-tetrahydro-benzo[b]thiophen-3-yl)-thiophen-2-yl-methanone To a stirred solution of 0.30 g (1.98 mmol) 3-oxo-3-thiophenyl-2-yl-propionitrile in 6 ml ethanol was added 0.21 ml (1.98 mmol) cyclohexanone, 64 mg (1.98 mmol) sulfur, and 0.17 ml (1.98 mmol) morpholine. The mixture was heated at 60° C. for 2 h and then poured onto water and extracted three times with ethyl acetate. The combined organic phases were dried over sodium sulfate and concentrated in vacuo. Trituration in ether afforded 0.52 g (98%) (2-amino-4,5,6,7-tetrahydro-benzo[b]thiophen-3-yl)-thiophen-2-yl-methanone as an orange solid. ES-MS m/e (%): 264 (M+H+, 100).

2,2,2-Trifluoro-1-(2-methyl-4-thiophen-2-yl-5,6,7,8-tetrahydro-benzo[4,5]thieno[2,3-b ]pyridin-3-yl)-ethanone To a stirred solution of 50 mg (0.19 mmol) (2-amino-4,5,6,7-tetrahydro-benzo[b]thiophen-3-yl)-thiophen-2-yl-methanone in 1.5 ml acetic acid was added 0.024 ml (0.20 mmol) of 1,1,1-trifluoro-pentane-2,4-dione and one drop of sulfuric acid. The mixture was then stirred at 100° C. for 10 minutes in a microwave and then concentrated in vacuo. Flash chromatography (heptane/ethyl acetate 9:1) afforded 17 mg (23%) 2,2,2-trifluoro-1-(2-methyl-4-thiophen-2-yl-5,6,7,8-tetrahydro-benzo[4,5]thieno[2,3-b]pyridin-3-yl)-ethanone as an orange oil. ES-MS m/e (%): 382 (M+H+, 100).

Example 7

1-(2-Methyl-4-thiophen-2-yl-5,6,7,8-tetrahydro-benzo[4,5]thieno[2,3-b]pyridin-3-yl)-ethanone To a stirred solution of 50 mg (0.19 mmol) (2-amino-4,5,6,7-tetrahydro-benzo[b]thiophen-3-yl)-thiophen-2-yl-methanone (the preparation of which is described in example 6) in 1.5 ml acetic acid was added 0.020 ml (0.21 mmol) of pentane-2,4-dione and one drop of sulfuric acid. The mixture was then stirred at 100° C. for 10 minutes in a microwave and then concentrated in vacuo. Flash chromatography (heptane/ethyl acetate 9:1) afforded 46 mg (74%) 1-(2-methyl-4-thiophen-2-yl-5,6,7,8-tetrahydro-benzo[4,5]thieno[2,3-b]pyridin-3-yl)-ethanone as a yellow oil. ES-MS m/e (%): 328 (M+H+, 100).

Example 8

2,2,2-Trifluoro-1-[4-(4-methoxy-phenyl)-2-methyl-5,6,7,8-tetrahydro-benzo[4,5]thieno[2,3-b]pyridin-3-yl)-ethanone (2-Amino-4,5,6,7-tetrahydro-benzo[b]thiophen-3-yl)-(4-methoxy-phenyl)-methanone To a stirred solution of 0.30 g (1.71 mmol) 3-(4-methoxy-phenyl)-3-oxo-propionitrile in 10 ml ethanol was added 0.17 ml (1.71 mmol) cyclohexanone, 53 mg (1.71 mmol) sulfur, and 0.14 ml (1.71 mmol) morpholine. The mixture was heated at 40° C. for the week end, and then poured onto water and extracted three times with ethyl acetate. The combined organic phases were dried over sodium sulfate and concentrated in vacuo. Trituration in ether afforded 0.51 g (85%) (2-amino-4,5,6,7-tetrahydro-benzo[b]thiophen-3-yl)-(4-methoxy-phenyl)-methanone as an orange solid. ES-MS m/e (%): 288 (M+H+, 100).

2,2,2-Trifluoro-1-[4-(4-methoxy-phenyl)-2-methyl-5,6,7,8-tetrahydro-benzo[4,5]thieno[2,3-b]pyridine-3-yl]-ethanone To a stirred solution of 50 mg (0.17 mmol) (2-amino-4,5,6,7-tetrahydro-benzo[b]thiophen-3-yl)-(4-methoxy-phenyl)-methanone in 1.5 ml acetic acid was added 0.021 ml (0.18 mmol) of 1,1,1-trifluoro-pentane-2,4-dione and one drop of sulfuric acid. The mixture was then stirred at 100° C. for 10 minutes in a microwave and then concentrated in vacuo. Flash chromatography (heptane/ethyl acetate 9:1) afforded 18 mg (25%) 2,2,2-trifluoro-1-[4-(4-methoxy-phenyl)-2-methyl-5,6,7,8-tetrahydro-benzo[4,5]thieno[2,3-b]pyridin-3-yl)-ethanone as a yellow oil. ES-MS m/e (%): 406 (M+H+, 100).

Example 9

1-[4-(4-Methoxy-phenyl)-2-methyl-5,6,7,8-tetrahydro-benzo[4,5]thieno[2,3-b]pyridin-3-yl)-ethanone To a stirred solution of 50 mg (0.17 mmol) (2-amino-4,5,6,7-tetrahydro-benzo[b]thiophen-3-yl)-(4-methoxy-phenyl)-methanone in 1.5 ml acetic acid was added 0.018 ml (0.18 mmol) of pentane-2,4-dione and one drop of sulfuric acid. The mixture was then stirred at 100° C. for 10 minutes in a microwave and then concentrated in vacuo. Flash chromatography (heptane/ethyl acetate 9:1) afforded 38 mg (62%) 1-[4-(4-methoxy-phenyl)-2-methyl-5,6,7,8-tetrahydro-benzo[4,5]thieno[2,3-b]pyridin-3-yl)-ethanone as a light yellow solid. ES-MS m/e (%): 352 (M+H+, 100).

Example 10

2,2,2-Trifluoro-1-[4-(4-methoxy-phenyl)-2-methyl-6,7-dihydro-5H-cyclopenta[4,5]thieno[2,3-b]pyridin-3-yl)-ethanone (2-Amino-5,6-dihydro-4H-cyclopenta[b]thiophen-3-yl)-(4-methoxy-phenyl)-methanone To a stirred solution of 0.30 g (1.71 mmol) 3-(4-methoxy-phenyl)-3-oxo-propionitrile in 10 ml ethanol was added 0.15 ml (1.71 mmol) cyclopentanone, 53 mg (1.71 mmol) sulfur, and 0.14 ml (1.71 mmol) morpholine. The mixture was heated at 40° C. for the week end, and then poured onto water and extracted three times with ethyl acetate. The combined organic phases were dried over sodium sulfate and concentrated in vacuo. Trituration in ether afforded 0.46 g (95%) (2-amino-5,6-dihydro-4H-cyclopenta[b]thiophen-3-yl)-(4-methoxy-phenyl)-methanone as a brown solid. ES-MS m/e (%): 274 (M+H+, 100).

2,2,2-Trifluoro-1-[4-(4-methoxy-phenyl)-2-methyl-6,7-dihydro-5H-cyclopenta[4,5]thieno[2,3-b]pyridin-3-yl)-ethanone To a stirred solution of 50 mg (0.18 mmol) (2-amino-5,6-dihydro-4H-cyclopenta[b]thiophen-3-yl)-(4-methoxy-phenyl)-methanone in 2 ml acetic acid was added 0.022 ml (0.18 mmol) of 1,1,1-trifluoro-pentane-2,4-dione and one drop of sulfuric acid. The mixture was then stirred at 100° C. for 10 minutes in a microwave and then concentrated in vacuo. Flash chromatography (heptane/ethyl acetate 9:1) afforded 20 mg (28%) 2,2,2-trifluoro-1-[4-(4-methoxy-phenyl)-2-methyl-6,7-dihydro-5H-cyclopenta[4,5]thieno[2,3-b]pyridin-3-yl)-ethanone as a white solid. ES-MS m/e (%): 392 (M+H+, 100).

Example 11

1-(2-methyl-4-phenyl-benzo[4,5[thieno[2,3-b]pyridin-3-yl)-ethanone (2-Amino-4,5,6,7-tetrahydro-benzo[b]thiophen-3-yl)-phenyl-methanone To a stirred solution of 0.60 g (4.13 mmol) 3-oxo-3-phenyl-propionitrile in 20 ml ethanol was added 0.43 ml (4.13 mmol) cyclohexanone, 133 mg (4.13 mmol) sulfur, and 0.36 ml (4.13 mmol) morpholine. The mixture was heated at 40° C. over the night and then poured onto water and extracted three times with ethyl acetate. The combined organic phases were dried over sodium sulfate and concentrated in vacuo. Trituration in ether afforded 1.041 g (98%) (2-Amino-4,5,6,7-tetrahydro-benzo[b]thiophen-3-yl)-phenyl-methanone as an orange solid. ES-MS m/e (%): 258 (M+H+, 100).

N-(3-Benzoyl-4,5,6,7-tetrahydro-benzo[b]thiophen-2-yl)-acetamide

To a stirred solution of 1.04 g (4.04 mmol) (2-Amino-4,5,6,7-tetrahydro-benzo[b]thiophen-3-yl)-phenyl-methanone in 25 ml acetic anhydride was added 0.2 ml pyridine. The mixture was heated at 50° C. for 35 minutes and then poured onto water and extracted three times with ethyl acetate. The combined organic phases were dried over sodium sulfate and concentrated in vacuo to afford 1.35 g (78%) N-(3-benzoyl-4,5,6,7-tetrahydro-benzo[b]thiophen-2-yl)-acetamide as an orange oil. ES-MS m/e (%): 300 (M+H+, 100).

N-(3-Benzoyl-benzo[b]thiophen-2-yl)-acetamide

To a stirred solution of 0.61 g (2.04 mmol) N-(3-Benzoyl-4,5,6,7-tetrahydro-benzo[b]thiophen-2-yl)-acetamide in 20 ml chloroform was added 1.2 g palladium on charcoal (10%). The mixture was stirred at room temperature for 15 minutes and then the solvent was removed in vacuo. The resulting powder was heated at 100° C. for 48 h and then suspended in ethyl acetate and dichloromethane. The suspension was filtered, and the organic phase was concentrated in vacuo to afford 0.26 g (44%) N-(3-benzoyl-benzo[b]thiophen-2-yl)-acetamide as a yellow solid. ES-MS m/e (%): 296 (M+H+, 100).

(2-Amino-benzo[b]thiophen-3-yl)-phenyl-methanone

To a stirred solution of 0.26 g (0.90 mmol) N-(3-benzoyl-benzo[b]thiophen-2-yl)-acetamide in 20 ml ethanol was added 1 ml aqueous sodium hydroxide (1 M). The mixture was heated at 85° C. for 1 hour and then poured onto water and extracted three times with ethyl acetate. The combined organic phases were dried over sodium sulfate and concentrated in vacuo. Flash chromatography (heptane/ethyl acetate 6:1) afforded 65 mg (25%) (2-amino-benzo[b]thiophen-3-yl)-phenyl-methanone as an orange solid. ES-MS m/e (%): 254 (M+H+, 100).

(2-methyl-4-phenyl-benzo[4,5]thieno[2,3-b]pyridin-3-yl)-ethanone

To a stirred solution of 32 mg (0.13 mmol) (2-amino-benzo[b]thiophen-3-yl)-phenyl-methanone in 2 ml acetic acid was added 0.09 ml (0.13 mmol) of pentane-2,4-dione and one drop of sulfuric acid. The mixture was then stirred at 100° C. for 10 minutes in a microwave and then concentrated in vacuo. Flash chromatography (heptane/ethyl acetate 6:1) afforded 21 mg (52%) (2-methyl-4-phenyl-benzo[4,5]thieno[2,3-b]pyridin-3-yl)-ethanone as a light yellow solid. ES-MS m/e (%): 318 (M+H+, 100).

Example 12

2,2,2-Trifluoro-1-(2-methyl-4-phenyl-benzo[4,5[thieno[2,3-b]pyridin-3-yl)-ethanone To a stirred solution of 32 mg (0.13 mmol) (2-amino-benzo[b]thiophen-3-yl)-phenyl-methanone (the preparation of which is described in example 11) in 2 ml acetic acid was added 0.016 ml (0.13 mmol) of 1,1,1-trifluoro-pentane-2,4-dione and one drop of sulfuric acid. The mixture was then stirred at 100° C. for 10 minutes in a microwave and then concentrated in vacuo. Flash chromatography (heptane/ethyl acetate 20:1) afforded 8 mg (17%) 2,2,2-trifluoro-1-(2-methyl-4-phenyl-benzo[4,5]thieno[2,3-b]pyridin-3-yl)-ethanone as a light yellow solid. ES-MS m/e (%): 372 (M+H+, 100).

Example 13

2,2,2-Trifluoro-1-[4-(4-methanesulfonyl-phenyl)-2-methyl-6,7-dihydro-5H-cyclopenta[4,5[thieno[2,3-b]pyridin-3-yl)-ethanone 3-(4-Methanesulfonyl-phenyl)-3-oxo-propionitrile To a stirred suspension of 1.0 g (3.61 mmol) (4-methanesulfonyl-phenyl)-acetyl bromide in 15 ml ethanol was added a solution of 0.47 g (7.22 mmol) potassium cyanide in 5 ml water. The mixture was then stirred at RT for 1 h, then acidified to ph=5-6 with aqueous HCl 1M and then extracted with ethyl acetate, The combined organic phases were dried over sodium sulfate and concentrated in vacuo to afford 0.29 g (37%) 3-(4-methanesulfonyl-phenyl)-3-oxo-propionitrile as a yellow solid. ES-MS m/e (%): 222 (M, 100).

(2-Amino-5,6-dihydro-4H-cyclopenta[b]thiophen-3-yl)-(4-methanesulfonyl-phenyl)-methanone To a stirred solution of 0.296 g (1.32 mmol) 3-(4-methanesulfonyl-phenyl)-3-oxo-propionitrile in 20 ml ethanol was added 0.12 ml (1.32 mmol) cyclopentanone, 43 mg (1.32 mmol) sulfur, and 0.12 ml (1.32 mmol) morpholine. The mixture was heated at 40° C. over night, and then poured onto water and extracted three times with ethyl acetate. The combined organic phases were dried over sodium sulfate and concentrated in vacuo. Trituration in ether afforded 0.37 g (87%) (2-amino-5,6-dihydro-4H-cyclopenta[b]thiophen-3-yl)-(4-methanesulfonyl-phenyl)-methanone as an orange solid. ES-MS m/e (%): 322 (M+H+, 100).

2,2,2-Trifluoro-1-[4-(4-methanesulfonyl-phenyl)-2-methyl-6,7-dihydro-5H-cyclopenta[4,5]thieno[2,3-b]pyridin-3-yl]-ethanone To a stirred solution of 50 mg (0.15 mmol) (2-amino-5,6-dihydro-4H-cyclopenta[b]thiophen-3-yl)-(4-methanesulfonyl-phenyl)-methanone in 2 ml acetic acid was added 0.020 ml (0.15 mmol) of 1,1,1-trifluoro-pentane-2,4-dione and one drop of sulfuric acid. The mixture was then stirred at 100° C. for 20 minutes in a microwave and then concentrated in vacuo. Preparative HPLC (30% $CH_3CN/H_2O$) afforded 18 mg (27%) 2,2,2-trifluoro-1-[4-(4-methanesulfonyl-phenyl)-2-methyl-6,7-dihydro-5H-cyclopenta[4,5]thieno[2,3-b]pyridin-3-yl)-ethanone as a light brown solid. ES-MS m/e (%): 440 (M+H+, 100).

Example 14

1-[4-(4-Methanesulfonyl-phenyl)-2-methyl-6,7-dihydro-5H-cyclopenta[4,5[thieno[2,3-b]pyridin-3-yl)-ethanone To a stirred solution of 50 mg (0.15 mmol) (2-amino-5,6-dihydro-4H-cyclopenta[b]thiophen-3-yl)-(4-methanesulfonyl-phenyl)-methanone (described above) in 2 ml acetic acid was added 0.011 ml (0.15 mmol) of pentane-2,4-dione and one drop of sulfuric acid. The mixture was then stirred at 100° C. for 10 minutes in a microwave and then concentrated in vacuo. Preparative HPLC (30% $CH_3CN/H_2O$) afforded 18 mg (30%) 1-[4-(4-methanesulfonylphenyl)-2-methyl-6,7-dihydro-5H-cyclopenta[4,5]thieno[2,3-b]pyridin-3-yl)-ethanone as a light brown solid. ES-MS m/e (%): 386 (M+H+, 100).

Example 15

1-(2,3,6-Trimethyl-4-phenyl-thieno[2,3-b]pyridin-5-yl)-ethanone (2-Amino-4,5-dimethyl-thiophen-3-yl)-phenyl-methanone To a stirred solution of 0.50 g (3.44 mmol) 3-oxo-3-phenyl-propionitrile in 10 ml ethanol was added 0.31 ml (3.44 mmol) butan-2-one, 110 mg (3.44 mmol) sulfur, and 0.30 ml (3.44 mmol) morpholine. The mixture was heated at 70° C. over the night and then poured onto water and extracted three times with ethyl acetate. The combined organic phases were dried over sodium sulfate and concentrated in vacuo. Trituration in ether afforded 0.71 g (89%) (2-Amino-4,5-dimethyl-thiophen-3-yl)-phenyl-methanone as a brown solid. ES-MS m/e (%): 232 (M+H+, 100).

1-(2,3,6-Trimethyl-4-phenyl-thieno[2,3-b]pyridin-5-yl)-ethanone

To a stirred solution of 70 mg (0.30 mmol) (2-Amino-4,5-dimethyl-thiophen-3-yl)-phenyl-methanone in 2 ml acetic acid was added 0.02 ml (0.30 mmol) of pentane-2,4-dione and one drop of sulfuric acid. The mixture was then stirred at 100° C. for 10 minutes in a microwave and then concentrated in vacuo. Preparative HPLC (30% $CH_3CN/H_2O$) afforded 10 mg (11%) 1-(2,3,6-trimethyl-4-phenyl-thieno[2,3-b]pyridine-5-yl)-ethanone as an orange solid. ES-MS m/e (%): 296 (M+H+, 100).

Example 16

2,2,2-Trifluoro-1-(2,3,6-trimethyl-4-phenyl-thieno[2,3-b]pyridin-5-yl)-ethanone To a stirred solution of 50 mg (0.22 mmol) (2-Amino-4,5-dimethyl-thiophen-3-yl)-phenyl-methanone (the preparation of which is described in example 15) in 2 ml acetic acid was added 0.03 ml (0.22 mmol) of 1,1,1-trifluoro-pentane-2,4-dione and one drop of sulfuric acid. The mixture was then stirred at 100° C. for 10 minutes in a microwave and then concentrated in vacuo. Preparative HPLC (30% $CH_3CN/H_2O$) afforded 8 mg (11%) 2,2,2-trifluoro-1-(2,3,6-trimethyl-4-phenyl-thieno[2,3-b]pyridine-5-yl)-ethanone as an orange solid. ES-MS m/e (%): 350 (M+H+, 100).

Example 17

2,2,2-Trifluoro-1-[4-(4-fluoro-phenyl)-2-methyl-6,7-dihydro-5H-cyclopenta[4,5]thieno[2,3-b]pyridin-3-yl]-ethanone 3-(4-Fluoro-phenyl)-3-oxo-propionitrile To a stirred suspension of 2.5 g (11.5 mmol) 2-bromo-1-(4-fluoro-phenyl)-ethanone (the preparation of which is described in example . . . ) in 40 ml ethanol was added a solution of 0.90 g (23 mmol) potassium cyanide in 9 ml water. The mixture was then stirred at RT for 2 h, then acidified to ph=5-6 with aqueous HCl 1M and then extracted with ethyl acetate. The combined organic phases were dried over sodium sulfate and concentrated in vacuo. Flash chromatography (heptane/ethyl acetate 6:1) afforded 0.11 g (6%) 3-(4-fluoro-phenyl)-3-oxo-propionitrile as a yellow solid.

(2-Amino-5,6-dihydro-4H-cyclopenta[b]thiophen-3-yl)-(4-fluoro-phenyl)-methanone

To a stirred solution of 0.11 g (0.67 mmol) 3-(4-fluoro-phenyl)-3-oxo-propionitrile in 4 ml ethanol was added 0.06 ml (0.67 mmol) cyclopentanone, 22 mg (0.67 mmol) sulfur, and 0.06 ml (0.67 mmol) morpholine. The mixture was heated at 60° C. for 2 h, and then poured onto water and extracted three times with ethyl acetate. The combined organic phases were dried over sodium sulfate and concentrated in vacuo. Trituration in ether afforded 0.17 g (98%) (2-amino-5,6-dihydro-4H-cyclopenta[b]thiophen-3-yl)-(4-fluoro-phenyl)-methanone as a red solid. ES-MS m/e (%): 262 (M+H+, 100).

2,2,2-Trifluoro-1-[4-(4-fluoro-phenyl)-2-methyl-6,7-dihydro-5H-cyclopenta[4,5]thieno[2,3-b]pyridin-3-yl]-ethanone To a stirred solution of 50 mg (0.19 mmol) (2-amino-5,6-dihydro-4H-cyclopenta[b]thiophen-3-yl)-(4-fluoro-phenyl)-methanone in 2 ml acetic acid was added 0.024 ml (0.19 mmol) of 1,1,1-trifluoro-pentane-2,4-dione and one drop of sulfuric acid. The mixture was then stirred at 100° C. for 10 minutes in a microwave and then concentrated in vacuo. Flash chromatography (heptane/ethyl acetate 9:1) afforded 10 mg (14%) 2,2,2-trifluoro-1-[4-(4-fluoro-phenyl)-2-methyl-6,7-dihydro-5H-cyclopenta[4,5]thieno[2,3-b]pyridin-3-yl]-ethanone as a light brown solid. ES-MS m/e (%): 380 (M+H+, 100).

Example 18

1-(4-Furan-2-yl-2-methyl-6,7-dihydro-5H-cyclopenta[4,5]thieno[2,3-b]pyridin-3-yl)-ethanone (2-Amino-5,6-dihydro-4H-cyclopenta[b]thiophen-3-yl)-furan-2-yl-methanone To a stirred solution of 1.0 g (7.40 mmol) 3-furan-2-yl-3-oxo-propionitrile in 20 ml ethanol was added 0.66 ml (7.40 mmol) cyclopentanone, 237 mg (7.40 mmol) sulfur, and 0.64 ml (7.40 mmol) morpholine. The mixture was heated at 70° C. for 2 h, and then poured onto water and extracted three times with ethyl acetate. The combined organic phases were dried over sodium sulfate and concentrated in vacuo. Trituration in ether afforded 1.87 g (90%) (2-amino-5,6-dihydro-4H-cyclopenta[b]thiophen-3-yl)-furan-2-yl-methanone as an orange solid. ES-MS m/e (%): 234 (M+H+, 100).

1-(4-Furan-2-yl-2-methyl-6,7-dihydro-5H-cyclopenta[4,5]thieno[2,3-b]pyridine-3-yl)-ethanone To a stirred solution of 50 mg (0.21 mmol) (2-amino-5,6-dihydro-4H-cyclopenta[b]thiophen-3-yl)-furan-2-yl-methanone in 2 ml acetic acid was added 0.016 ml (0.21 mmol) of pentane-2,4-dione and one drop of sulfuric acid. The mixture was then stirred at 100° C. for 10 minutes in a microwave and then concentrated in vacuo. Preparative HPLC (30% CH$_3$CN/H$_2$0) afforded 20 mg (31%) 1-(4-furan-2-yl-2-methyl-6,7-dihydro-5H-cyclopenta[4,5]thieno[2,3-b]pyridin-3-yl)-ethanone as a yellow solid. ES-MS m/e (%): 298 (M+H+, 100).

Example 19

2,2,2-Trifluoro-1-(4-furan-2-yl-2-methyl-6,7-dihydro-5H-cyclopenta[4,5]thieno[2,3-b]pyridin-3-yl)-ethanone To a stirred solution of 50 mg (0.21 mmol) (2-amino-5,6-dihydro-4H-cyclopenta[b]thiophen-3-yl)-furan-2-yl-methanone (the preparation of which is described in example 18) in 2 ml acetic acid was added 0.027 ml (0.21 mmol) of 1,1,1-trifluoro-pentane-2,4-dione and one drop of sulfuric acid. The mixture was then stirred at 100° C. for 10 minutes in a microwave and then concentrated in vacuo. Preparative HPLC (30% CH$_3$CN/H$_2$0) afforded 19 mg (25%) 2,2,2-trifluoro-1-(4-furan-2-yl-2-methyl-6,7-dihydro-5H-cyclopenta[4,5]thieno[2,3-b]pyridin-3-yl)-ethanone as a yellow solid. ES-MS m/e (%): 352 (M+H+, 72).

Example 20

2,2,2-Trifluoro-1-(6-methyl-4-phenyl-thieno[2,3-b]pyridin-5-yl)-ethanone (2-amino-thiophen-3-yl)-phenyl-methanone Following a procedure described in J. Med. Chem. 2002, 45, 382-389; 1.45 g (10 mmol) 3-oxo-3-phenyl-propionitrile, 0.76 g (5.0 mmol) [1,4]dithiane-2,5-diol, 0.40 ml (10 mmol) diethylamine and 5 ml ethanol were charged in a sealed tube. The reaction mixture was heated at 50° C. for 6 h. The tube was then placed in a fridge (about 4° C.) for the night, and the product was collected by filtration and dried under vacuum to afford 0.42 g (23%) (2-amino-thiophen-3-yl)-phenyl-methanone as a light brown crystals. ES-MS m/e (%): 204 (M+H+, 100).

2,2,2-Trifluoro-1-(6-methyl-4-phenyl-thieno[2,3-b]pyridin-5-yl)-ethanone

To a stirred solution of 50 mg (0.24 mmol) (2-amino-thiophen-3-yl)-phenyl-methanone in 2 ml acetic acid was added 0.031 ml (0.24 mmol) of 1,1,1-trifluoro-pentane-2,4-dione and one drop of sulfuric acid. The mixture was then stirred at 100° C. for 10 minutes in a microwave and then concentrated in vacuo. Preparative HPLC (30% CH$_3$CN/H$_2$0) afforded 13 mg (17%) 2,2,2-trifluoro-1-(6-methyl-4-phenyl-thieno[2,3-b]pyridin-5-yl)-ethanone as a yellow oil. ES-MS m/e (%): 322 (M+H+, 100).

Example 21

1-(2-Chloro-6-methyl-4-phenyl-thieno[2,3-b]pyridin-5-yl)-2,2,2-trifluoro-ethanone (2-amino-5-chloro-thiophen-3-yl)-phenyl-methanone To a stirred solution of 0.1 g (0.49 mmol) (2-amino-thiophen-3-yl)-phenyl-methanone (the preparation of which is described in example 20) in 10 ml dichloromethane at 0° C. was added 68 mg (0.49 mmol) N-chloro-succinimide (NCS). The mixture was then stirred from 0° C. to RT over night, and then poured onto water and extracted three times with ethyl acetate. The combined organic phases were dried over sodium sulfate and concentrated in vacuo. Flash chromatography (heptane/ethyl acetate 3:1) afforded 40 mg (34%) (2-amino-5-chloro-thiophen-3-yl)-phenyl-methanone as a yellow solid.

1-(2-Chloro-6-methyl-4-phenyl-thieno[2,3-b]pyridin-5-yl)-2,2,2-trifluoro-ethanone To a stirred solution of 30 mg (0.13 mmol) (2-amino-5-chloro-thiophen-3-yl)-phenyl-methanone in 2 ml acetic acid was added 0.016 ml (0.13 mmol) of 1,1,1-trifluoro-pentane-2,4-dione and one drop of sulfuric acid. The mixture was then stirred at 70° C. for 10 minutes in a microwave and then concentrated in vacuo. Preparative HPLC (30% CE-CN/H$_2$0) afforded 10 mg (23%) 1-(2-chloro-6-methyl-4-phenyl-thieno[2,3-b]pyridin-5-yl)-2,2,2-trifluoro-ethanone as a light brown solid. ES-MS m/e (%): 356 (M+H+, 100).

Example 22

2,2,2-Trifluoro-1-[4-(4-fluoro-phenyl)-6-methyl-thieno[2,3-b]pyridin-5-yl]-ethanone (2-amino-thiophen-3-yl)-(4-fluoro-phenyl)-methanone Following a procedure described in J. Med. Chem. 2002, 45, 382-389; 0.44 g (2.7 mmol) 3-(4-fluoro-phenyl)-3-oxo-propionitrile (the preparation of which is described in example 17), 0.33 g (2.15 mmol) [1,4]dithiane-2,5-diol, 0.16 ml (2.15 mmol) diethyl-amine and 5 ml ethanol were charged in a sealed tube. The reaction mixture was heated at 50° C. for 6 h. The tube was then placed in a fridge (about 4° C.) for the night, and the product was collected by filtration and dried under vacuum to afford 0.41 g (69%) (2-amino-thiophen-3-yl)-(4-fluoro-phenyl)-methanone as a light brown crystals.

2,2,2-Trifluoro-1-[4-(4-fluoro-phenyl)-6-methyl-thieno[2,3-b]pyridin-5-yl]-ethanone To a stirred solution of 30 mg (0.13 mmol) (2-amino-thiophen-3-yl)-(4-fluoro-phenyl)-methanone in 1 ml acetic acid was added 0.017 ml (0.13 mmol) of 1,1,1-trifluoro-pentane-2,4-dione and one drop of sulfuric acid. The mixture was then stirred at 100° C. for 15 minutes in a microwave and then concentrated in vacuo. Preparative HPLC (30% $CH_3CN/H_2O$) afforded 8 mg (17%) 2,2,2-trifluoro-1-[4-(4-fluoro-phenyl)-6-methyl-thieno[2,3-b]pyridin-5-yl]-ethanone as a yellow oil. ES-MS m/e (%): 340 (M+H+, 100).

Example 23

1-(2-Methyl-4-phenyl-9-thia-1,7-diaza-fluoren-3-yl)-ethanone

2 Amino-3-benzoyl-4,7-dihydro-5H-thieno[2,3-c]pyridine-6-carboxylic acid tert-butyl ester To a stirred solution of 2.0 g (13.78 mmol) 3-oxo-3-phenyl-propionitrile in 50 ml ethanol was added 2.74 g (13.78 mmol) 4-oxo-piperidine-1-carboxylic acid tert-butyl ester, 442 mg (13.78 mmol) sulfur, and 1.2 ml (13.78 mmol) morpholine. The mixture was heated at 60° C. for 3 h, and then poured onto water and extracted three times with ethyl acetate. The combined organic phases were dried over sodium sulfate and concentrated in vacuo. Crystallisation in ethyl acetate afforded 3.60 g (73%) 2-amino-3-benzoyl-4,7-dihydro-5H-thieno[2,3-c]pyridine-6-carboxylic acid tert-butyl ester as yellow crystals. ES-MS m/e (%): 359 (M+H+, 48).

3-Acetyl-2-methyl-4-phenyl-5,8-dihydro-6H-9-thia-1,7-diaza-fluorene-7-carboxylic acid tert-butyl ester To a stirred solution of 0.50 g (1.39 mmol) 2-amino-3-benzoyl-4,7-dihydro-5H-thieno[2,3-c]pyridine-6-carboxylic acid tert-butyl ester in 6 ml acetic acid was added 0.19 ml (1.89 mmol) of pentane-2,4-dione and two drops of sulfuric acid. The mixture was then stirred at 100° C. for 25 minutes in a microwave and then concentrated in vacuo. Flash chromatography (heptane/ethyl acetate 4:1) afforded 70 mg (12%) 3-acetyl-2-methyl-4-phenyl-5,8-dihydro-6H-9-thia-1,7-diaza-fluorene-7-carboxylic acid tert-butyl ester as a yellow oil. ES-MS m/e (%): 423 (M+H+, 100).

1-(2-Methyl-4-phenyl-5,6,7,8-tetrahydro-9-thia-1,7-diaza-fluoren-3-yl)-ethanone

To a stirred solution of 70 mg (0.16 mmol) 3-acetyl-2-methyl-4-phenyl-5,8-dihydro-6H-9-thia-1,7-diaza-fluorene-7-carboxylic acid tert-butyl ester in 3 ml dicloromethane was added 0.2 ml trifluoroacetic acid. The mixture was stirred over night at RT, and then poured onto an aqueous solution of $NaHCO_3$, and extracted three times with ethyl acetate. The combined organic phases were dried over sodium sulfate and concentrated in vacuo to afford 48 mg (94%) 1-(2-methyl-4-phenyl-5,6,7,8-tetrahydro-9-thia-1,7-diaza-fluoren-3-yl)-ethanone as a yellow solid. ES-MS m/e (%): 323 (M+H+, 100).

1-(2-methyl-4-phenyl-9-thia-1,7-diaza-fluoren-3-yl)-ethanone

To a stirred solution of 0.70 g (2.17 mmol) 1-(2-methyl-4-phenyl-5,6,7,8-tetrahydro-9-thia-1,7-diaza-fluoren-3-yl)-ethanone in 10 ml diphenylethylene was added 325 mg palladium on charcoal 10%. The mixture was stirred over night at 150° C., and then poured onto ethyl acetate (about 150 ml), and extracted three times aqueous HCl (1M). The combined aqueous phases were basified with $K_2CO_3$ until ph=8, and then the product was extracted with ethyl acetate. The combined organic phase were dried over sodium sulfate and concentrated in vacuo. Flash chromatography (heptane/ethyl acetate 1:1) afforded 75 mg (11%) 1-(2-methyl-4-phenyl-9-thia-1,7-diaza-fluoren-3-yl)-ethanone as a light yellow solid. ES-MS m/e (%): 319 (M+H+, 100).

Example 24

1-[2-Chloro-4-(4-fluoro-phenyl)-6-methyl-thieno[2,3-b]pyridin-5-yl]-2,2,2-trifluoro-ethanone (2-Amino-5-chloro-thiophen-3-yl)-(4-fluoro-phenyl)-methanone To a stirred solution of 0.26 g (1.18 mmol) (2-amino-thiophen-3-yl)-(4-fluoro-phenyl)-methanone (the preparation of which is described in example 22) in 10 ml dichloromethane at 0° C. was added 164 mg (1.18 mmol) N-chlorosuccinimide (NCS). The mixture was then stirred from 0° C. to RT over night, and then poured onto water and extracted three times with ethyl acetate. The combined organic phases were dried over sodium sulfate and concentratedin vacuo. Flash chromatography (heptane/ethyl acetate 4:1) afforded 95 mg (32%) (2-amino-5-chloro-thiophen-3-yl)-(4-fluoro-phenyl)-methanone as a yellow solid. ES-MS m/e (%): 256 (M+H+, 100).

1-[2-Chloro-4-(4-fluoro-phenyl)-6-methyl-thieno[2,3-b]pyridin-5-yl]-2,2,2-trifluoro-ethanone To a stirred solution of 50 mg (0.19 mmol) (2-amino-5-chloro-thiophen-3-yl)-(4-fluoro-phenyl)-methanone in 2 ml acetic acid was added 0.025 ml (0.19 mmol) of 1,1,1-trifluoro-pentane-2,4-dione and one drop of sulfuric acid. The mixture was then stirred at 70° C. for 10 minutes in a microwave and then concentrated in vacuo. Flash chromatography (heptane/ethyl acetate 9:1) afforded 8 mg (11%) 1-[2-chloro-4-(4-fluoro-phenyl)-6-methyl-thieno[2,3-b]pyridin-5-yl]-2,2,2-trifluoro-ethanone as an orange oil. ES-MS m/e (%): 374 (M+H+, 100).

Example 25

Cyclopropyl-(2-methyl-4-phenyl-6,7-dihydro-5H-cyclopenta[4,5]thieno[2,3-b]pyridin-3-yl)-methanone To a stirred solution of 60 mg (0.24 mmol) (2-amino-5,6-dihydro-4H-cyclopenta[b]thiophen-3-yl)-phenyl-methanone (the preparation of which is described in example 3) in 2 ml acetic acid was added 41 mg (0.32 mmol) of 1-cyclopropyl-butane-1,3-dione (prep. described in the patent DE 94-4404059) and one drop of sulfuric acid. The mixture was then stirred at 100° C. for 10 minutes in a microwave and then concentrated in vacuo. Preparative HPLC (30% CH$_3$CN/H$_2$0) afforded 27 mg (33%) cyclopropyl-(2-methyl-4-phenyl-6,7-dihydro-5H-cyclopenta[4,5]thieno[2,3-b]pyridin-3-yl)-methanone as a light brown oil. ES-MS m/e (%): 334 (M+H$^+$, 100).

Example 26

Cyclopropyl-(6-methyl-4-phenyl-thieno[2,3-b]pyridin-5-yl)-methanone

To a stirred solution of 60 mg (0.29 mmol) (2-amino-thiophen-3-yl)-phenyl-methanone (the preparation of which is described in example 20) in 2 ml acetic acid was added 50 mg (0.39 mmol) of 1-cyclopropyl-butane-1,3-dione and one drop of sulfuric acid. The mixture was then stirred at 100° C. for 10 minutes in a microwave and then concentrated in vacuo. Flash chromatography (heptane/ethyl acetate 6:1) afforded 7 mg (8%) cyclopropyl-(6-methyl-4-phenyl-thieno[2,3-b]pyridin-5-yl)-methanone as a colorless oil. ES-MS m/e (%): 294 (M+H$^+$, 100).

Example 27

Cyclopropyl-(2-methyl-4-thiophen-2-yl-6,7-dihydro-5H-cyclopenta[4,5]thieno[2,3-b]pyridin-3-yl)-methanone To a stirred solution of 60 mg (0.24 mmol) (2-amino-5,6-dihydro-4H-cyclopenta[b]thiophen-3-yl)-thiophen-2-yl-methanone) (the preparation of which is described in example 2) in 2 ml acetic acid was added 40 mg (0.32 mmol) of 1-cyclopropyl-butane-1,3-dione and one drop of sulfuric acid. The mixture was then stirred at 100° C. for 10 minutes in a microwave and then concentrated in vacuo. Preparative HPLC (30% CH$_3$CN/H$_2$O) afforded 15 mg (19%) cyclopropyl-(2-methyl-4-thiophen-2-yl-6,7-dihydro-5H-cyclopenta[4,5]thieno[2,3-b]pyridin-3-yl)-methanone as a light brown oil. ES-MS m/e (%): 340 (M+H$^+$, 100).

Example 28

Cyclopropyl-(4-furan-2-yl-2-methyl-6,7-dihydro-5H-cyclopenta[4,5]thieno[2,3-b]pyridin-3-yl)-methanone To a stirred solution of 60 mg (0.26 mmol) (2-amino-5,6-dihydro-4H-cyclopenta [b]thiophen-3-yl)-furan-2-yl-methanone (the preparation of which is described in example 18) in 2 ml acetic acid was added 43 mg (0.34 mmol) of 1-cyclopropyl-butane-1,3-dione and one drop of sulfuric acid. The mixture was then stirred at 100° C. for 10 minutes in a microwave and then concentrated in vacuo. Preparative HPLC (30% CH$_3$CN/H$_2$O) afforded 17 mg (21%) cyclopropyl-(4-furan-2-yl-2-methyl-6,7-dihydro-5H-cyclopenta[4,5]thieno[2,3-b]pyridin-3-yl)-methanone as a light brown solid. ES-MS m/e (%): 324 (M+H$^+$, 100).

Example 29

Cyclopropyl-[(4-(3,4-dichloro-phenyl)-2-methyl-6,7-dihydro-5H-cyclopenta [4,5]thieno[2,3-b]pyridin-3-yl)-methanone To a stirred solution of 60 mg (0.19 mmol) (2-amino-5,6-dihydro-4H-cyclopenta[b]thiophen-3-yl)-(3,4-dichloro-phenyl)-methanone (the preparation of which is described in example 1) in 2 ml acetic acid was added 32 mg (0.25 mmol) of 1-cyclopropyl-butane-1,3-dione and one drop of sulfuric acid. The mixture was then stirred at 100° C. for 10 minutes in a microwave and then concentrated in vacuo. Preparative HPLC (30% CH$_3$CN/H$_2$0) afforded 24 mg (31%) cyclopropyl-[(4-(3,4-dichloro-phenyl)-2-methyl-6,7-dihydro-5H-cyclopenta[4,5]thieno [2,3-b]pyridin-3-yl)-methanone as a light brown solid. ES-MS m/e (%): 402 (M+H$^+$, 100).

Example 30

Cyclopropyl-[(4[(3,4-dichloro-phenyl)-2-methyl-5,6,7,8-tetrahydro-benzo[4,5]thieno [2,3-b]pyridin-3-yl)]-methanone (2-Amino-4,5,6,7-tetrahydro-benzo[b]thiophen-3-yl)-(3,4-dichloro-phenyl)-methanone To a stirred solution of 0.30 g (1.40 mmol) 3-(3,4-dichloro-phenyl)-3-oxo-propionitrile in 10 ml ethanol was added 0.14 ml (1.40 mmol) cyclohexanone, 43 mg (1.40 mmol) sulfur, and 0.12 ml (1.40 mmol) morpholine. The mixture was heated at 40° C. for 48 h and then poured onto water and extracted three times with ethyl acetate. The combined organic phases were dried over sodium sulfate and concentrated in vacuo. Trituration in ether afforded 0.478 g (78%) (2-amino-4,5,6,7-tetrahydro-benzo[b]thiophen-3-yl)-(3,4-dichloro-phenyl)-methanone as an orange solid. ES-MS m/e (%): 326 (M+H$^+$, 100).

Cyclopropyl-[(4-(3,4-dichloro-phenyl)-2-methyl-5,6,7,8-tetrahydro-benzo[4,5]thieno [2,3-b]pyridin-3-yl)]-methanone To a stirred solution of 60 mg (0.18 mmol) (2-amino-4,5,6,7-tetrahydro-benzo[b]thiophen-3-yl)-(3,4-dichloro-phenyl)-methanone in 2 ml acetic acid was added 31 mg (0.24 mmol) of 1-cyclopropyl-butane-1,3-dione and one drop of sulfuric acid. The mixture was then stirred at 100° C. for 10 minutes in a microwave and then concentrated in vacuo. Preparative HPLC (30% CH$_3$CN/H$_2$0) afforded 18 mg (23%) cyclopropyl-[(4-(3,4-dichloro-phenyl)-2-methyl-5,6,7,8-tetrahydro-benzo[4,5]thieno [2,3-b]pyridin-3-yl)]-methanone as a light brown solid. ES-MS m/e (%): 416 (M+H$^+$, 100).

Example 31

Cyclopropyl-[4-(4-methoxy-phenyl)-2-methyl-6,7-dihydro-5H-cyclopenta [4,5]thieno[2,3-b]pyridin-3-yl)]-methanone To a stirred solution of 60 mg (0.22 mmol) (2-amino-5,6-dihydro-4H-cyclopenta[b]thiophen-3-yl)-(4-methoxy-phenyl)-methanone (the preparation of which is described in example 10) in 2 ml acetic acid was added 37 mg (0.29 mmol) of 1-cyclopropyl-butane-1,3-dione and one drop of sulfuric acid. The mixture was then stirred at 100° C. for 10 minutes in a microwave and then concentrated in vacuo. Preparative HPLC (30% CH₃CN/H₂O) afforded 17 mg (22%) cyclopropyl-[4-(4-methoxy-phenyl)-2-methyl-6,7-dihydro-5H-cyclopenta[4,5]thieno [2,3-b]pyridin-3-yl)-methanone as a light brown solid. ES-MS m/e (%): 364 (M+H$^+$, 100).

Example 32

Cyclopropyl-[4-(4-methoxy-phenyl)-2-methyl-5,6,7,8-tetrahydro-benzo[4,5]thieno[2,3-b]pyridin-3-yl)]-methanone To a stirred solution of 60 mg (0.21 mmol) (2-amino-4,5,6,7-tetrahydro-benzo[b]thiophen-3-yl)-(4-methoxy-phenyl)-methanone (the preparation of which is described in example 8) in 2 ml acetic acid was added 35 mg (0.28 mmol) of 1-cyclopropyl-butane-1,3-dione and one drop of sulfuric acid. The mixture was then stirred at 100° C. for 10 minutes in a microwave and then concentrated in vacuo. Preparative HPLC (30% CH₃CN/H₂O) afforded 25 mg (32%) cyclopropyl-[4-(4-methoxy-phenyl)-2-methyl-5,6,7,8-tetrahydro-benzo[4,5]thieno[2,3-b]pyridin-3-yl)-methanone as a light brown oil. ES-MS m/e (%): 378 (M+H$^+$, 100).

Example 33

4-(3-Cyclopropanecarbonyl-2-methyl-6,7-dihydro-5H-cyclopenta[4,5]thieno[2,3-b]pyridin-4-yl)-benzoic acid methyl ester 4-(2-Amino-5,6-dihydro-4H-cyclopenta[b]thiophene-3-carbonyl)-benzoic acid methyl ester
To a stirred solution of 0.30 g (1.47 mmol) 4-(2-cyanoacetyl)-benzoic acid methyl ester in 10 ml ethanol was added 0.13 ml (1.47 mmol) cyclopentanone, 46 mg (1.47 mmol) sulfur, and 0.12 ml (1.47 mmol) morpholine. The mixture was heated at 40° C. for 72 h and then poured onto water and extracted three times with ethyl acetate. The combined organic phases were dried over sodium sulfate and concentrated in vacuo. Trituration in ether afforded 0.53 g (98%) 4-(2-Amino-5,6-dihydro-4H-cyclopenta[b]thiophene-3-carbonyl)-benzoic acid methyl ester as a brown solid. ES-MS m/e (%): 302 (M+H$^+$, 100).

4-(3-Cyclopropanecarbonyl-2-methyl-6,7-dihydro-5H-cyclopenta[4,5]thieno[2,3-b]pyridin-4-yl)-benzoic acid methyl ester
To a stirred solution of 60 mg (0.20 mmol) 4-(2-amino-5,6-dihydro-4H-cyclopenta[b]thiophene-3-carbonyl)-benzoic acid methyl ester in 2 ml acetic acid was added 33 mg (0.26 mmol) of 1-cyclopropyl-butane-1,3-dione and one drop of sulfuric acid. The mixture was then stirred at 100° C. for 10 minutes in a microwave and then concentrated in vacuo. Preparative HPLC (30% CH₃CN/H₂O) afforded 22 mg (28%) 4-(3-cyclopropanecarbonyl-2-methyl-6,7-dihydro-5H-cyclopenta[4,5]thieno[2,3-b]pyridin-4-yl)-benzoic acid methyl ester as a light brown oil. ES-MS m/e (%): 392 (M+H$^+$, 100).

Example 34

4-(3-Cyclopropanecarbonyl-2-methyl-5,6,7,8-tetrahydro-benzo[4,5]thieno[2,3-b]pyridin-4-yl)-benzoic acid methyl ester 4-(2-Amino-4,5,6,7-tetrahydro-benzo[b]thiophene-3-carbonyl)-benzoic acid methyl ester
To a stirred solution of 0.30 g (1.47 mmol) 4-(2-cyanoacetyl)-benzoic acid methyl ester in 10 ml ethanol was added 0.15 ml (1.47 mmol) cyclohexanone, 46 mg (1.47 mmol) sulfur, and 0.12 ml (1.47 mmol) morpholine. The mixture was heated at 40° C. for 72 h and then poured onto water and extracted three times with ethyl acetate. The combined organic phases were dried over sodium sulfate and concentrated in vacuo. Trituration in ether afforded 0.45 g (97%) 4-(2-amino-4,5,6,7-tetrahydro-benzo[b]thiophene-3-carbonyl)-benzoic acid methyl ester as a brown solid. ES-MS m/e (%): 316 (M+H$^{30}$, 100).

4-(3-Cyclopropanecarbonyl-2-methyl-5,6,7,8-tetrahydro-benzo[4,5]thieno[2,3-b]pyridin-4-yl)-benzoic acid methyl ester
To a stirred solution of 60 mg (0.19 mmol) 4-(2-Amino-4,5,6,7-tetrahydro-benzo[b]thiophene-3-carbonyl)-benzoic acid methyl ester in 2 ml acetic acid was added 32 mg (0.25 mmol) of 1-cyclopropyl-butane-1,3-dione and one drop of sulfuric acid. The mixture was then stirred at 100° C. for 10 minutes in a microwave and then concentrated in vacuo. Preparative HPLC (30% CH₃CN/H₂O) afforded 28 mg (37%) 4-(3-cyclopropanecarbonyl-2-methyl-5,6,7,8-tetrahydro-benzo[4,5]thieno[2,3-b]pyridin-4-yl)-benzoic acid methyl ester as a light pink solid. ES-MS m/e (%): 406 (M+H$^+$, 100).

Example 35

4-(3-Cyclopropanecarbonyl-2-methyl-6,7,8,9-tetrahydro-H-10-thia-1-aza-benzo [a]azulen-4-yl)-benzoic acid methyl ester 4-(2-Amino-5,6,7,8-tetrahydro-4H-cyclohepta[b]thiophene-3-carbonyl)-benzoic acid methyl ester
To a stirred solution of 0.30 g (1.47 mmol) 4-(2-cyanoacetyl)-benzoic acid methyl ester in 10 ml ethanol was added 0.17 ml (1.47 mmol) cycloheptanone, 46 mg (1.47 mmol) sulfur, and 0.13 ml (1.47 mmol) morpholine. The mixture was heated at 40° C. for 72 h and then poured onto water and extracted three times with ethyl acetate. The combined organic phases were dried over sodium sulfate and concentrated in vacuo. Trituration in ether afforded 0.10 g (22%) 4-(2-amino-5,6,7,8-tetrahydro-4H-cyclohepta[b]thiophene-3-carbonyl)-benzoic acid methyl ester as an orange solid. ES-MS m/e (%): 330 (M+H$^+$, 100).

4-(3-Cyclopropanecarbonyl-2-methyl-6,7,8,9-tetrahydro-5H-10-thia-1-aza-benzo[a]azulen-4-yl)-benzoic acid methyl ester
To a stirred solution of 20 mg (0.06 mmol) 4-(2-Amino-5,6,7,8-tetrahydro-4H-cyclohepta[b]thiophene-3-carbonyl)-benzoic acid methyl ester in 1 ml acetic acid was added 10 mg (0.06 mmol) of 1-cyclopropyl-butane-1,3-dione and one drop of sulfuric acid. The mixture was then stirred at 100° C. for 10 minutes in a microwave and then concentrated in vacuo. Preparative HPLC (30% CH₃CN/H₂O) afforded 11 mg (44%) 4-(3-cyclopropanecarbonyl-2-methyl-6,7,8,9-tetrahydro-5H-10-thia-1-aza-benzo[a]azulen-4-yl)-benzoic acid methyl ester as a light yellow solid. ES-MS m/e (%): 420 (M+H$^+$, 100).

Example 36

Cyclopropyl-[4-(3,4-dichloro-phenyl)-2-methyl-6,7,8,9-tetrahydro-5H-10-thia-1-aza-benzo[a]azulen-3-yl)-methanone (2-Amino-5,6,7,8-tetrahydro-4H-cyclohepta[b]thiophen-3-yl)-(3,4-dichloro-phenyl)-methanone To a stirred solution of 0.30 g (1.40 mmol) 3-(3,4-dichloro-phenyl)-3-oxo-propionitrile in 10 ml ethanol was added 0.15 ml (1.40 mmol) cycloheptanone, 43 mg (1.40 mmol) sulfur, and 0.12 ml (1.40 mmol) morpholine. The mixture was heated at 40° C. for 72 h and then poured onto water and extracted three times with ethyl acetate. The combined organic phases were dried over sodium sulfate and concentrated in vacuo. Trituration in ether afforded 0.12 g (26%) (2-amino-5,6,7,8-tetrahydro-4H-cyclohepta[b]thiophen-3-yl)-(3,4-dichloro-phenyl)-methanone as a yellow oil. ES-MS m/e (%): 340 (M+H$^+$, 100).

Cyclopropyl-[4-(3,4-dichloro-phenyl)-2-methyl-6,7,8,9-tetrahydro-5H-10-thia-1-aza-benzo[a]azulen-3-yl)-methanone To a stirred solution of 36 mg (0.11 mmol) (2-amino-5,6,7,8-tetrahydro-4H-cyclohepta[b]thiophen-3-yl)-(3,4-dichloro-phenyl)-methanone in 2 ml acetic acid was added 18 mg (0.11 mmol) of 1-cyclopropyl-butane-1,3-dione and one drop of sulfuric acid. The mixture was then stirred at 100° C. for 10 minutes in a microwave and then concentrated in vacuo. Preparative HPLC (30% CH$_3$CN/H$_2$O) afforded 10 mg (19%) cyclopropyl-[4-(3,4-dichlorophenyl)-2-methyl-6,7,8,9-tetrahydro-5H-10-thia-1-aza-benzo[a]azulen-3-yl)-methanone as a light yellow oil. ES-MS m/e (%): 430 (M+H$^+$, 100).

Example 37

Cyclopropyl-(2-methyl-4-phenyl-9-thia-1,7-diaza-fluoren-3-yl)-methanone

Cyclopropyl-(2-methyl-4-phenyl-5,6,7,8-tetrahydro-9-thia-1,7-diaza-fluoren-3-yl)-methanone To a stirred solution of 1.0 g (2.79 mmol) 2-amino-3-benzoyl-4,7-dihydro-5H-thieno[2,3-c]pyridine-6-carboxylic acid tert-butyl ester (the preparation of which is described in example 23) in 15 ml acetic acid was added 0.70 g (5.55 mmol) of 1-cyclopropyl-butane-1,3-dione and three drops of sulfuric acid. The mixture was then stirred at 100° C. for 30 minutes and then concentrated in vacuo. Flash chromatography (dichloromethane/methanol 95:5) afforded 0.47 g (48%) cyclopropyl-(2-methyl-4-phenyl-5,6,7,8-tetrahydro-9-thia-1,7-diaza-fluoren-3-yl)-methanone as a brown oil. ES-MS m/e (%): 349 (M+H$^+$, 100).

Cyclopropyl-(2-methyl-4-phenyl-9-thia-1,7-diaza-fluoren-3-yl)-methanone

To a stirred solution of 0.46 g (1.32 mmol) cyclopropyl-(2-methyl-4-phenyl-5,6,7,8-tetrahydro-9-thia-1,7-diaza-fluoren-3-yl)-methanone in 7 ml diphenylethylene was added 230 mg palladium on charcoal 10%. The mixture was stirred over night at 150° C., and then poured onto ethyl acetate (about 150 ml), and extracted three times aqueous HCl (1M). The combined aqueous phases were basified with K$_2$CO$_3$ until ph=8, and then the product was extracted with ethyl acetate. The combined organic phase were dried over sodium sulfate and concentrated in vacuo. Flash chromatography (heptane/ethyl acetate 1:1) afforded 35 mg (8%) cyclopropyl-(2-methyl-4-phenyl-9-thia-1,7-diaza-fluoren-3-yl)-methanone as a light yellow solid. ES-MS m/e (%): 345 (M+H$^+$, 100).

Example 38

3-Acetyl-2-methyl-4-phenyl-5,8-dihydro-6H-9-thia-1,7-diaza-fluorene-7-carboxylic acid methyl ester To a stirred solution of 50 mg (0.15 mmol) 1-(2-methyl-4-phenyl-5,6,7,8-tetrahydro-9-thia-1,7-diaza-fluoren-3-yl)-ethanone (the preparation of which is described in example 23) in 5 ml dichloromethane was added 0.02 ml (0.022 mmol) methyl chloroformate and 32 mg (0.022 mmol) potassium carbonate. The mixture was stirred at RT for 1 h and then poured onto water and extracted three times with ethyl acetate. The combined organic phases were dried over sodium sulfate and concentrated in vacuo. Flash chromatography (heptane/ethyl acetate 1:1) afforded 33 mg (56%) 3-Acetyl-2-methyl-4-phenyl-5,8-dihydro-6H-9-thia-1,7-diaza-fluorene-7-carboxylic acid-methyl ester as a light yellow solid. ES-MS m/e (%): 381 (M+H$^+$, 100);

Example 39

Cyclopropyl-(2-methyl-4-phenyl-5,8-dihydro-6H-7-oxa-9-thia-1-aza-fluoren-3-yl)-methanone (2-Amino-4,7-dihydro-5H-thieno[2,3-c]pyran-3-yl)-phenyl-methanone To a stirred solution of 0.725 g (5.00 mmol) 3-oxo-3-phenyl-propionitrile in 5 ml ethanol was added 0.50 g (5.00 mmol) tetrahydro-pyran-4-one, 160 mg (5.00 mmol) sulfur, and 0.44 ml (5.00 mmol) morpholine. The mixture was heated at 55° C. for 2 h and then poured onto water and extracted three times with ethyl acetate. The combined organic phases were dried over sodium sulfate and concentrated in vacuo. Trituration in ether afforded 0.75 g (58%) (2-amino-4,7-dihydro-5H-thieno[2,3-c]pyran-3-yl)-phenyl-methanone as a light yellow solid. ES-MS m/e (%): 260 (M+H$^+$, 100).

Cyclopropyl-(2-methyl-4-phenyl-5,8-dihydro-6H-7-oxa-9-thia-1-aza-fluoren-3-yl)-methanone To a stirred solution of 100 mg (0.38 mmol) (2-amino-4,7-dihydro-5H-thieno[2,3-c]pyran-3-yl)-phenyl-methanone in 5 ml acetic acid was added 73 mg (0.57 mmol) of 1-cyclopropyl-butane-1,3-dione (prep. described in the patent DE 94-4404059) and one drop of sulfuric acid. The mixture was then stirred at 70° C. for 2 hours and then concentrated in vacuo. Flash chromatography (heptane/ethyl acetate 3:1) afforded 50 mg (37%) cyclopropyl-(2-methyl-4-phenyl-5,8-dihydro-6H-7-oxa-9-thia-1-aza-fluoren-3-yl)-methanone as a yellow solid. ES-MS m/e (%): 350 (M+H$^+$, 100).

Example 40

Cyclopropyl-(6-methyl-4-piperidin-1-yl-2,3-dihydro-1H-8-thia-7-aza-cyclopenta[a]inden-5-yl)-methanone 2-Amino-5,6-dihydro-4H-cyclopenta[b]thiophene-3-carbonitrile To a stirred solution of 6.28 g (0.095 mol) malonitrile in 100 ml ethanol was added 8.00 g (0.095 mol) cyclopentanone, 3.04 g (0.095 mol) sulfur, and 8.29 ml (0.095 mol) morpholine. The mixture was heated at 80° C. for 2 h and then poured onto water and extracted three times with ethyl acetate. The combined organic phases were dried over sodium sulfate and concentrated in vacuo. Flash chromatography (heptane/ethyl acetate 3:1) afforded 4.89 g (31%) 2-amino-5,6-dihydro-4H-cyclopenta[b]thiophene-3-carbonitrile as a light brown solid. ES-MS m/e (%): 165 (M+H$^+$, 100).

(4-Amino-6-methyl-2,3-dihydro-1H-8-thia-7-aza-cyclopenta[a]inden-5-yl)-cyclopropyl-methanone To a stirred solution of 0.30 g (1.83 mmol) of 2-amino-5,6-dihydro-4H-cyclopenta[b]thiophene-3-carbonitrile in 6 ml toluene was added 0.30 g (2.14 mmol) 1-cyclopropyl-3-methoxy-but-2-en-1-one and 3 mg of p-toluenesulfonic acid. The mixture was heated at reflux for 2 hours, concentrated in vacuo, partitioned between ethyl acetate and water. The combined organic phases were dried over sodium sulfate and evaporated to dryness. The residue was taken up in n-butyl acetate 6 ml and 1.018 g (3.91 mmol) tin (IV) chloride was heated under reflux for 30 minute and allowed to cool. The mixture was partitioned between aqueous sodium hydroxide and ethyl acetate. Flash chromatography (heptane/ethyl acetate 3:1) afforded 25 mg (5%) (4-amino-6-methyl-2,3-dihydro-1H-8-thia-7-aza-cyclopenta[a]inden-5-yl)-cyclopropyl-methanone as a white solid. ES-MS m/e (%): 273 (M+H$^+$, 100).

Cyclopropyl-(6-methyl-4-piperidin-1-yl-2,3-dihydro-1H-8-thia-7-aza-cyclopenta[a]inden-5-yl)-methanone To a stirred solution of 12 mg (0.044 mmol) of (4-amino-6-methyl-2,3-dihydro-1H-8-thia-7-aza-cyclopenta[a]inden-5-yl)-cyclopropyl-methanone in 2 ml DMF was added 3.0 mg (0.066 mmol) NaH (55% in oil). After 20 minutes, 10 □l (0.044 mmol) of 1,5-dibromo-pentane and stirring was continued at RT over the night. The mixture was poured onto water and extracted three times with ethyl acetate. The combined organic phases were dried over sodium sulfate and concentrated in vacuo. Flash chromatography (heptane/ethyl acetate 6:1) afforded 8 mg (54%) cyclopropyl-(6-methyl-4-piperidin-1-yl-2,3-dihydro-1H-8-thia-7-aza-cyclopenta[a]inden-5-yl)-methanone as a white solid. ES-MS m/e (%): 341 (M+H$^+$, 100).

Example 41

1-(6-Methyl-2,4-diphenyl-thieno[2,3-b]pyridin-5-yl)-ethanone

N-(3-Benzoyl-5-bromo-thiophen-2-yl)-acetamide

To a stirred solution of 1.00 g (4.92 mmol) of (2-amino-thiophen-3-yl)-phenyl-methanone (the preparation of which is described in example 20) in 20 ml CFCl$_2$ at 0° C. was added 0.92 g (5.18 mmol) NBS (N-bromo succinimide) in one portion. After 10 minutes, 4.65 ml (49.2 mmol) of acetic anhydride, 0.68 ml (4.92 mmol) of Et$_3$N and 0.30 g (2.45 mmol) of DMAP were added. Stirring was continued at RT for 2 hours, the mixture was poured onto water and extracted three times with CH$_2$Cl$_2$. The combined organic phases were dried over sodium sulfate and concentrated in vacuo. Flash chromatography (heptane/CH$_2$Cl$_2$ 1:1) afforded 0.85 g (53%) N-(3-benzoyl-5-bromo-thiophen-2-yl)-acetamide as a light brown solid. ES-MS m/e (%): 324, 326 (M+H$^+$, 100).

N-(3-Benzoyl-5-phenyl-thiophen-2-yl)-acetamide

A stirred solution of 0.448 g (1.38 mmol) of N-(3-benzoyl-5-bromo-thiophen-2-yl) acetamide in 20 ml toluene and 10 ml EtOH was degassed with argon. Tetrakis-(triphenylphosphine) palladium (0) (0.320 g, 0.27 mmol), phenyl boronic acid (0.194 g, 1.59 mmol) and 20 ml of an aqueous solution of Na$_2$CO$_3$ 1N were added. The mixture was heated at 90° C. for 1 hour before cooling down to RT, filtered through Celite and concentrated. The mixture was extracted with ethyl acetate and aq. NaHCO$_3$. The combined organic phases were dried over sodium sulfate and concentrated in vacuo. Flash chromatography (heptane/ethyl acetate 6:1) afforded 0.393 g (88%) N-(3-benzoyl-5-phenyl-thiophen-2-yl)-acetamide as a light yellow solid. ES-MS m/e (%): 322 (M+H$^+$, 100).

(2-Amino-5-phenyl-thiophen-3-yl)-phenyl-methanone

To a stirred solution of 0.393 g (1.22 mmol) of N-(3-benzoyl-5-phenyl-thiophen-2-yl)-acetamide in 15 ml EtOH was added 2.5 ml of aq. NaOH (4N). The reaction mixture stirred at RT for 1 hour, and then poured onto an aq. solution of NH$_4$Cl sat. and the product was extracted with ethyl acetate. The combined organic phases were dried over sodium sulfate and concentrated in vacuo to yield 0.45 g (98%) of (2-amino-5-phenyl-thiophen-3-yl)-phenyl-methanone as a light brown solid. ES-MS m/e (%): 280 (M+H$^+$, 100).

1-(6-Methyl-2,4-diphenyl-thieno[2,3-b]pyridin-5-yl)-ethanone

To a stirred solution of 55 mg (0.197 mmol) (2-amino-5-phenyl-thiophen-3-yl)-phenyl-methanone-in-5 ml-acetic acid was added 0.016 ml (0.239 mmol) of pentane-2,4-dione and one drop of sulfuric acid. The mixture was then stirred at 100° C. for 10 minutes in a microwave and then concentrated in vacuo. Preparative HPLC (30% CH$_3$CN/H$_2$O) afforded 19 mg (28%) 1-(6-methyl-2,4-diphenyl-thieno[2,3-b]pyridin-5-yl)-ethanone as a light grey solid. ES-MS m/e (%): 344 (M+H$^+$, 100).

Example 42

Cyclopropyl-(6-Methyl-2,4-diphenyl-thieno[2,3-b]pyridin-5-yl)-methanone

To a stirred solution of 0.130 g (0.465 mmol) (2-amino-5-phenyl-thiophen-3-yl)-phenyl-methanone in 7 ml acetic acid was added 62 mg (0.491 mmol) of 1-cyclopropyl-butane-1,3-dione and one drop of sulfuric acid. The mixture was then stirred at 110° C. for 20 minutes in a microwave and then concentrated in vacuo. Preparative HPLC (30% CH$_3$CN/H$_2$0) afforded 29 mg (17%) cyclopropyl-(6-methyl-2,4-diphenyl-thieno[2,3-b]pyridin-5-yl)-methanone as a light yellow powder. ES-MS m/e (%): 370 (M+H$^+$, 100).

The invention claimed is:
1. A compound of formula I

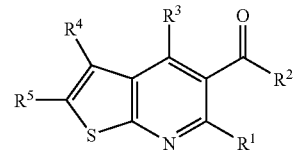

wherein
R$^1$ is hydrogen, C$_1$-C$_7$-alkyl, or C$_3$-C$_8$-cycloalkyl;
R$^2$ is C$_1$-C$_7$-alkyl, CF$_3$, C$_3$-C$_8$-cycloalkyl, optionally substituted aryl or optionally substituted heteroaryl having 5 to 9 ring atoms, wherein the substituents are selected from the group consisting of halo, C$_1$-C$_7$-alkoxy, C$_1$-C$_7$-alkylsulfonyl, and —C(O)O—C$_1$-C$_7$-alkyl;
R$^3$ is —NR$^a$R$^b$; optionally substituted heterocycloalkyl having 3 to 8 ring atoms, optionally substituted aryl, or optionally substituted heteroaryl having 5 to 9 ring atoms, wherein the substituents are selected from the group consisting of halo, C$_1$-C$_7$-alkoxy, C$_1$-C$_7$-alkylsulfonyl, and —C(O)O—C$_1$-C$_7$-alkyl;

R⁴ is hydrogen, or C₁-C₇-alkyl; and
R⁵ is hydrogen, halo, C₁-C₇-alkyl, optionally substituted aryl or optionally substituted heteroaryl having 5 to 9 ring atoms, wherein the substituents are selected from the group consisting of halo, C₁-C₇-alkyl, C₁-C₇-alkoxy, and —C(O)O—C₁-C₇-alkyl;
or R⁵ together with R⁴ forms a ring selected from the group consisting of C₅-C₇-cycloalkyl, phenyl, pyridinyl, and pyrimidinyl which are optionally substituted or by one or more halo, cyano, C₁-C₇-alkylsulfonyl, C₁-C₇-alkyl, C₁-C₇-haloalkyl, C₁-C₇-alkoxy, C₁-C₇-haloalkoxy, or —C(O)O—C₁-C₇-alkyl; or heterocycloalkyl having 5 to 7 rings atoms, optionally substituted by one or more cyano, C₁-C₇-alkyl, C₁-C₇-alkoxy, or C(O)O—C₁-C₇alkyl;
Rᵃ and Rᵇ are each independently C₁-C₇-alkyl, or Rᵃ and Rᵇ, together with the nitrogen atom to which they are attached, form a unsubstituted piperidine;
or a pharmaceutically acceptable salt thereof.

2. A compound of claim 1, wherein R² is C₁-C₇-alkyl.

3. A compound of claim 2, selected from the group consisting of:
   1-(2-Methyl-4-phenyl-6,7-dihydro-5H-cyclopenta[4,5]thieno[2,3-b]pyridin-3-yl)-ethanone;
   1-(2-Methyl-4-thiophen-2-yl-6,7-dihydro-5H-cyclopenta[4,5]thieno[2,3-b]pyridin-3-yl)-ethanone;
   1-(2-Methyl-4-thiophen-2-yl-5,6,7,8-tetrahydro-benzo[4,5]thieno[2,3-b]pyridin-3-yl)-ethanone;
   1-[4-(4-Methoxy-phenyl)-2-methyl-5,6,7,8-tetrahydro-benzo[4,5]thieno[2,3-b]pyridin-3-yl]-ethanone;
   1-(2-methyl-4-phenyl-benzo[4,5]thieno[2,3-b]pyridin-3-yl)-ethanone;
   1-[4-(4-Methanesulfonyl-phenyl)-2-methyl-6,7-dihydro-5H-cyclopenta[4,5]thieno[2,3-b]pyridin-3-yl)-ethanone;
   1-(2,3,6-Trimethyl-4-phenyl-thieno[2,3-b]pyridin-5-yl)-ethanone;
   1-(4-Furan-2-yl-2-methyl-6,7-dihydro-5H-cyclopenta[4,5]thieno[2,3-b]pyridin-3-yl)-ethanone;
   1-(2-Methyl-4-phenyl-9-thia-1,7-diaza-fluoren-3-yl)-ethanone;
   3-Acetyl-2-methyl-4-phenyl-5,8-dihydro-6H-9-thia-1,7-diaza-fluorene-7-carboxylic acid methyl ester; and
   1-(6-Methyl-2,4-diphenyl-thieno[2,3-b]pyridin-5-yl)-ethanone.

4. A compound of claim 1, wherein R² is CF₃.

5. A compound of claim 4, selected from the group consisting of:
   1-[4-(3,4-Dichloro-phenyl)-2-methyl-6,7-dihydro-5H-cyclopenta[4,5]thieno[2,3-b]pyridin-3-yl]-2,2,2-trifluoro-ethanone;
   2,2,2-Trifluoro-1-(2-methyl-4-thiophen-2-yl-6,7-dihydro-5H-cyclopenta[4,5]thieno[2,3-b]pyridin-3-yl)-ethanone;
   2,2,2-Trifluoro-1-(2-methyl-4-phenyl-6,7-dihydro-5H-cyclopenta[4,5]thieno[2,3-b]pyridin-3-yl)-ethanone;
   2,2,2-Trifluoro-1-(2-methyl-4-thiophen-2-yl-5,6,7,8-tetrahydro-benzo[4,5]thieno[2,3-b]pyridin-3-yl)-ethanone;
   2,2,2-Trifluoro-1-[4-(4-methoxy-phenyl)-2-methyl-5,6,7,8-tetrahydro-benzo[4,5]thieno[2,3-b]pyridin-3-yl)-ethanone;
   2,2,2-Trifluoro-1-[4-(4-methoxy-phenyl)-2-methyl-6,7-dihydro-5H-cyclopenta[4,5]thieno[2,3-b]pyridin-3-yl)-ethanone;
   2,2,2-Trifluoro-1-(2-methyl-4-phenyl-benzo[4,5]thieno[2,3-b]pyridin-3-yl)-ethanone; and
   2,2,2-Trifluoro-1-[4-(4-methanesulfonyl-phenyl)-2-methyl-6,7-dihydro-5H-cyclopenta[4,5]thieno[2,3-b]pyridin-3-yl)-ethanone.

6. A compound of claim 4, selected from the group consisting of
   2,2,2-Trifluoro-1-(2,3,6-trimethyl-4-phenyl-thieno[2,3-b]pyridin-5-yl)-ethanone;
   2,2,2-Trifluoro-1-[4-(4-fluoro-phenyl)-2-methyl-6,7-dihydro-5H-cyclopenta[4,5]thieno[2,3-b]pyridin-3-yl]-ethanone;
   2,2,2-Trifluoro-1-(4-furan-2-yl-2-methyl-6,7-dihydro-5H-cyclopenta[4,5]thieno[2,3-b]pyridin-3-yl)-ethanone;
   2,2,2-Trifluoro-1-(6-methyl-4-phenyl-thieno[2,3-b]pyridin-5-yl)-ethanone;
   1-(2-Chloro-6-methyl-4-phenyl-thieno[2,3-b]pyridin-5-yl)-2,2,2-trifluoro-ethanone;
   2,2,2-Trifluoro-1-[4-(4-fluoro-phenyl)-6-methyl-thieno[2,3-b]pyridin-5-yl]-ethanone; and
   1-[2-Chloro-4-(4-fluoro-phenyl)-6-methyl-thieno[2,3-b]pyridin-5-yl]-2,2,2-trifluoro-ethanone.

7. A compound of claim 1, wherein R² is C₃-C₈-cycloalkyl.

8. A compound of claim 7, selected from the group consisting of:
   Cyclopropyl-(2-methyl-4-phenyl-6,7-dihydro-5H-cyclopenta[4,5]thieno[2,3-b]pyridin-3-yl)-methanone;
   Cyclopropyl-(6-methyl-4-phenyl-thieno[2,3-b]pyridin-5-yl)-methanone;
   Cyclopropyl-(2-methyl-4-thiophen-2-yl-6,7-dihydro-5H-cyclopenta[4,5]thieno[2,3-b]pyridin-3-yl)-methanone;
   Cyclopropyl-(4-furan-2-yl-2-methyl-6,7-dihydro-5H-cyclopenta[4,5]thieno[2,3-b]pyridin-3-yl)-methanone;
   Cyclopropyl-[(4-(3,4-dichloro-phenyl)-2-methyl-6,7-dihydro-5H-cyclopenta[4,5]thieno[2,3-b]pyridin-3-yl)-methanone;
   Cyclopropyl-[(4-(3,4-dichloro-phenyl)-2-methyl-5,6,7,8-tetrahydro-benzo[4,5]thieno [2,3-b]pyridin-3-yl)]-methanone;
   Cyclopropyl-[4-(4-methoxy-phenyl)-2-methyl-6,7-dihydro-5H-cyclopenta[4,5]thieno[2,3-b]pyridin-3-yl)]-methanone; and
   Cyclopropyl-[4-(4-methoxy-phenyl)-2-methyl-5,6,7,8-tetrahydro-benzo[4,5]thieno[2,3-b]pyridin-3-yl)]-methanone.

9. A compound of claim 7, selected from the group consisting of
   4-(3-Cyclopropanecarbonyl-2-methyl-6,7-dihydro-5H-cyclopenta[4,5]thieno[2,3-b]pyridin-4-yl)-benzoic acid methyl ester,
   4-(3-Cyclopropanecarbonyl-2-methyl-5,6,7,8-tetrahydro-benzo[4,5]thieno[2,3-b]pyridin-4-yl)-benzoic acid methyl ester,
   4-(3-Cyclopropanecarbonyl-2-methyl-6,7,8,9-tetrahydro-5H-10-thia-1-aza-benzo[a]azulen-4-yl)-benzoic acid methyl ester,
   Cyclopropyl-[4-(3,4-dichloro-phenyl)-2-methyl-6,7,8,9-tetrahydro-5H-10-thia-1-aza-benzo[a]azulen-3-yl]-methanone;
   Cyclopropyl-(2-methyl-4-phenyl-9-thia-1,7-diaza-fluoren-3-yl)-methanone;
   Cyclopropyl-(2-methyl-4-phenyl-5,8-dihydro-6H-7-oxa-9-thia-1-aza-fluoren-3-yl)-methanone;
   Cyclopropyl-(6-methyl-4-piperidin-1-yl-2,3-dihydro-1H-8-thia-7-aza-cyclopenta[a]inden-5-yl)-methanone; and
   Cyclopropyl-(6-Methyl-2,4-diphenyl-thieno[2,3-b]pyridin-5-yl)-methanone.

10. A compound of claim 1, wherein $R^4$ is $C_1$-$C_7$-alkyl.

11. A compound of claim 1, wherein $R^1$ is $C_1$-$C_7$-alkyl.

12. A compound of claim 1, wherein $R^3$ is phenyl optionally substituted with a substituent selected from the group consisting of halo, $C_1$-$C_7$-alkoxy, $C_1$-$C_7$-alkylsulfonyl, and —C(O)O—$C_1$-$C_7$-alkyl.

13. A compound of claim 1, wherein $R^3$ is thienyl optionally substituted with a substituent selected from the group consisting of halo, $C_1$-$C_7$-alkoxy, $C_1$-$C_7$-alkylsulfonyl, and —C(O)O—$C_1$-$C_7$-alkyl.

14. A compound of claim 1, wherein $R^3$ is furanyl optionally substituted with a substituent selected from the group consisting of halo, $C_1$-$C_7$-alkoxy, $C_1$-$C_7$-alkylsulfonyl, and —C(O)O—$C_1$-$C_7$-alkyl.

15. A compound of claim 1, wherein $R^1$ is $C_1$-$C_7$-alkyl;

$R^2$ is $C_1$-$C_7$-alkyl, $C_1$-$C_7$-haloalkyl, or $C_3$-$C_8$-cycloalkyl;

$R^3$ is heterocycloalkyl having 3 to 8 ring atoms, aryl or heteroaryl having 5 to 9 ring atoms, each of which are optionally substituted by one or more substituent(s) selected from the group consisting of halo, $C_1$-$C_7$-alkoxy, $C_1$-$C_7$-alkylsulfonyl, and —C(O)O—$C_1$-$C_7$-alkyl;

$R^4$ is hydrogen or $C_1$-$C_7$-alkyl; and $R^5$ is hydrogen, halo, $C_1$-$C_7$-alkyl, or aryl;

or $R^5$ together with $R^4$ forms a ring selected from the group consisting of $C_5$-$C_7$-cycloalkyl, phenyl pyridinyl, and pyrimidinyl which are optionally substituted or by one or more halo, cyano, $C_1$-$C_7$-alkylsulfonyl, $C_1$-$C_7$-alkyl, $C_1$-$C_7$-haloalkyl, $C_1$-$C_7$-alkoxy, $C_1$-$C_7$-haloalkoxy, or —C(O)O—$C_1$-$C_7$-alkyl, or heterocycloalkyl having 5 to 7 ring atoms optionally substituted by one or more cyano, $C_1$-$C_7$-alkyl, $C_1$-$C_7$alkoxy, or C(O)O—$C_1$-$C_7$alkyl;

or a pharmaceutically acceptable salt thereof.

16. A compound of claim 1, comprising formula Ia:

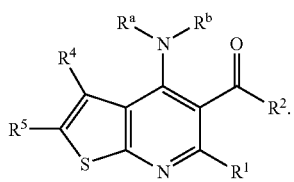

(Ia)

17. A compound of claim 16, wherein $R^1$ is methyl, ethyl, propyl, i-propyl, butyl, i-butyl, or t-butyl.

18. A compound of claim 16, wherein $R^2$ is methyl, ethyl, propyl, i-propyl, butyl, i-butyl, t-butyl, cyclopropyl, cyclobutyl, cyclopentyl, cyclohexyl, phenyl, or $CF_3$.

19. A compound of claim 16, wherein $R^4$ is hydrogen or methyl.

20. A compound of claim 16, wherein $R^5$ is $C_1$-$C_7$-alkyl, aryl, halo, or hydrogen.

21. A compound of claim 16, wherein $R^4$ and $R^5$, together with the nitrogen atom to which they are attached, form $C_5$-$C_7$-cycloalkyl, phenyl, or pyridinyl optionally substituted by —C(O)O—$C_1$-$C_7$-alkyl.

22. A compound of claim 1, comprising formula Ic:

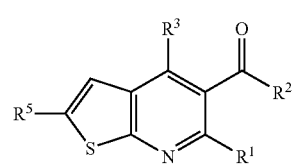

(Ic)

wherein $R^5$ is optionally substituted aryl or heteroaryl having 5 to 9 ring atoms, wherein the substituents are selected from the group consisting of halo, cyano, $C_1$-$C_7$-alkyl, $C_1$-$C_7$-alkoxy, $C_1$-$C_7$and —C(O)O—$C_1$-$C_7$-alkyl.

23. A compound of claim 22, wherein $R^1$ is methyl, ethyl, propyl, i-propyl, butyl, i-butyl, or t-butyl.

24. A compound of claim 22, wherein $R^2$ is methyl, ethyl, propyl, i-propyl, butyl, i-butyl, t-butyl, cyclopropyl, cyclobutyl, cyclopentyl, cyclohexyl, phenyl, or $CF_3$.

25. A compound of claim 22, wherein $R^3$ is phenyl optionally substituted by one or more halo, $C_1$-$C_7$-alkoxy, or —C(O)O—$C_1$-$C_7$-alkyl; thiophenyl; furanyl; piperidine; or morpholine.

26. A pharmaceutical composition comprising a compound of formula I

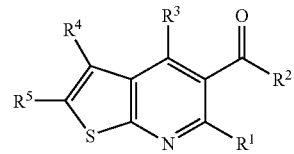

wherein $R^1$ is hydrogen, $C_1$-$C_7$-alkyl, or $C_3$-$C_8$-cycloalkyl;

$R^2$ is $C_1$-$C_7$-alkyl, $CF_3$, $C_3$-$C_8$-cycloalkyl, optionally substituted aryl or optionally substituted heteroaryl having 5 to 9 ring atoms, wherein the substituents are selected from the group consisting of halo, $C_1$-$C_7$-alkoxy, $C_1$-$C_7$-alkylsulfonyl, and —C(O)O—$C_1$-$C_7$-alkyl;

$R^3$ is —$NR^aR^b$; optionally substituted heterocycloalkyl having 3 to 8 ring atoms, optionally substituted aryl, or optionally substituted heteroaryl having 5 to 9 ring atoms, wherein the substituents are selected from the group consisting of halo, $C_1$-$C_7$-alkoxy, $C_1$-$C_7$-alkylsulfonyl, and —C(O)O—$C_1$-$C_7$-alkyl, or heterocycloalkyl having 5 to 7 ring atoms optionally substituted by one or more cyano, $C_1$-$C_7$alkyl, $C_1$-$C_7$alkoxy, or —C(O)O—$C_1$-$C_7$alkyl;

$R^4$ is hydrogen, or $C_1$-$C_7$-alkyl; and $R^5$ is hydrogen, halo, $C_1$-$C_7$-alkyl, —$NR^aR^b$, optionally substituted heteroaryl having 5 to 9 ring atoms, wherein the substituents are selected from the group consisting of halo, cyano, $C_1$-$C_7$-alkyl, $C_1$-$C_7$-alkoxy, and —C(O)O—$C_1$-$C_7$-alkyl;

or $R^5$ together with $R^4$ forms a ring selected from the group consisting of $C_5$-$C_7$-cycloalkyl, heterocycloalkyl, phenyl, pyridinyl, and pyrimidinyl which are optionally substituted or by one or more halo, cyano, $C_1$-$C_7$-alkylsulfonyl, $C_1$-$C_7$-alkyl, $C_1$-$C_7$-haloalkyl, $C_1$-$C_7$-alkoxy, $C_1$-$C_7$-haloalkoxy, or —C(O)O—$C_1$-$C_7$-alkyl;

$R^a$ and $R^b$ are each independently $C_1$-$C_7$-alkyl, or $R^a$ and $R^b$, together with the nitrogen atom to which they are attached, form an unsubstituted piperidine;

or a pharmaceutically acceptable salt thereof and a pharmaceutically acceptable carrier.

27. A pharmaceutical composition of claim 26, wherein the compound is a compound of formula Ia

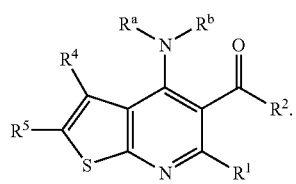

(Ia)

28. A pharmaceutical composition of claim 26, wherein the compound is a compound of formula Ic

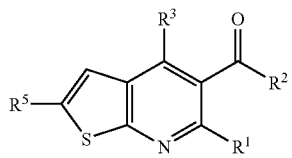

(Ic)

wherein $R^5$ is selected from the group consisting of $C_2$-$C_7$-alkenyl and optionally substituted aryl or heteroaryl having 5 to 9 ring atoms, wherein the substituents are selected from the group consisting of halo, cyano, $C_1$-$C_7$-alkyl, $C_1$-$C_7$-alkoxy, and —C(O)O—$C_1$-$C_7$-alkyl.

* * * * *